(12) United States Patent
Ouchida et al.

(10) Patent No.: US 9,212,387 B2
(45) Date of Patent: Dec. 15, 2015

(54) METHOD FOR DETECTION OF GENES TARGETED BY MICRORNA

(75) Inventors: Mamoru Ouchida, Okayama (JP); Sachio Ito, Okayama (JP)

(73) Assignee: National University Corporation Okayama University, Okayama-shi, Okayama (JP)

( * ) Notice: Subject to any disclaimer, the term of this patent is extended or adjusted under 35 U.S.C. 154(b) by 61 days.

(21) Appl. No.: 13/704,604

(22) PCT Filed: Jun. 15, 2011

(86) PCT No.: PCT/JP2011/063636
§ 371 (c)(1),
(2), (4) Date: Dec. 14, 2012

(87) PCT Pub. No.: WO2011/158847
PCT Pub. Date: Dec. 22, 2011

(65) Prior Publication Data
US 2013/0089866 A1    Apr. 11, 2013

(30) Foreign Application Priority Data
Jun. 17, 2010    (JP) ................................. 2010-137924

(51) Int. Cl.
*C12Q 1/68*    (2006.01)

(52) U.S. Cl.
CPC ................ *C12Q 1/68* (2013.01); *C12Q 1/6834* (2013.01); *C12Q 1/6886* (2013.01); *C12Q 2600/178* (2013.01)

(58) Field of Classification Search
CPC ........................................................ C12Q 1/68
USPC ........................................................ 435/6.1
See application file for complete search history.

(56) References Cited

U.S. PATENT DOCUMENTS

| | | | |
|---|---|---|---|
| 5,241,060 A * | 8/1993 | Engelhardt et al. ........ | 536/25.32 |
| 7,932,047 B2 | 4/2011 | Ridder et al. | |
| 8,685,946 B2 * | 4/2014 | Hutvagner et al. ............ | 514/55 |
| 2004/0175732 A1 | 9/2004 | Rana | |
| 2005/0249791 A1 | 11/2005 | Hobbs et al. | |
| 2007/0072229 A1 * | 3/2007 | Bialozynski et al. ............. | 435/6 |
| 2010/0029501 A1 | 2/2010 | Samal | |

FOREIGN PATENT DOCUMENTS

WO    WO 2010/033818 A2    3/2010

OTHER PUBLICATIONS

Orom, U. A. and Lund, A. H., "Isolation of microRNA targets using biotinylated synthetic microRNAs", Methods, 2007, vol. 43, pp. 162-165.

Nonne, N. et al., "Tandem affinity purification of miRNA target mRNAs (TAP-Tar)", Nucleic Acids Research, Dec. 2009, vol. 38, No. 4, pp. 1-5, doi:10.1093/nar/gkp1100.

Zheng, W. et al., "Identification of microRNA target genes in vivo", Mol Biotechnol., Sep. 2010, vol. 47, pp. 200-204.

Kim, T. et al., "Preparation and Characterization of Platinum—ruthenium Bimetallic Nanoparticles Using Reverse Microemulsions for Fuel Cell Catalyst", J. Oleo Science, 2007, 56(10), pp. 553-562.

* cited by examiner

*Primary Examiner* — Ardin Marschel
(74) *Attorney, Agent, or Firm* — Don D. Cha; Hamilton DeSanctis & Cha, LLP

(57) ABSTRACT

Provided is a detection kit for detecting target genes of miRNA. Also provided is a method of detecting target genes of miRNA in a simple manner without the need for performing a transfection operation of a gene into cells via a vector. The detection kit is a detection kit for target genes of microRNA, including a cell extraction reagent, and a labeling reagent for microRNA or labeled microRNA, and further including a reaction reagent for the labeling substance for microRNA. mRNA corresponding to target genes of miRNA can be easily pulled down by producing a cell extract under mild conditions, adding labeled miRNA to the cell extract, and recovering the labeling substance. cDNA is produced from the pulled down mRNA to detect target genes of miRNA.

15 Claims, 15 Drawing Sheets

1: UNTREATED
2: anti-GFP-LNA
3: anti-miR183-LNA

M: DNA marker (100-500bp)
1: miR-19a
2: Negative control

1 : miR183      2 : miR183-Natural      3 : Negative control (SEQ ID NO: 1)      (SEQ ID NO: 1)      (SEQ ID NO: 10)

uauggcacugguagaauucacu ●    uauggc---ac uggua ga auucacu ●    auccgcgcgauaguacguauu ●
gaa_cccgugaccaucuuaagu    aauaccg ggaa gccau __uaagug    uuuaggcgcguaucaugcau (SEQ ID NO: 2)      (SEQ ID NO: 9)      (SEQ ID NO: 11)

VIL2    PPP2CA    RREB1    BCL2L11    PDCD4    LATS2

M : DNA marker (100-500bp)
1 : miR183
2 : miR183-Natural
3 : Negative control

RSU1    ING3    DNMT3A    BRMS1L

SEQUENCE LISTING

```
<160> NUMBER OF SEQ ID NOS: 11

<210> SEQ ID NO 1
<211> LENGTH: 22
<212> TYPE: RNA
<213> ORGANISM: Artificial
<220> FEATURE:
<223> OTHER INFORMATION: Synthesized RNA for a miR-183

<400> SEQUENCE: 1
uauggcacug guagaauuca cu                                            22

<210> SEQ ID NO 2
<211> LENGTH: 22
<212> TYPE: RNA
<213> ORGANISM: Artificial
<220> FEATURE:
<223> OTHER INFORMATION: Synthesized RNA for a guide strand of a miR-183

<400> SEQUENCE: 2
ugaauucuac cagugccaca ag                                            22
```

```
<210> SEQ ID NO 3
<211> LENGTH: 22
<212> TYPE: RNA
<213> ORGANISM: Artificial
<220> FEATURE:
<223> OTHER INFORMATION: Synthesized RNA for a let-7b

<400> SEQUENCE: 3
ugagguagua gguugugugg uu                                              22

<210> SEQ ID NO 4
<211> LENGTH: 22
<212> TYPE: RNA
<213> ORGANISM: Artificial
<220> FEATURE:
<223> OTHER INFORMATION: Synthesized RNA for a guide strand of a let-7b

<400> SEQUENCE: 4
ccacacaacc uacuaccuua ag                                              22

<210> SEQ ID NO 5
<211> LENGTH: 22
<212> TYPE: RNA
<213> ORGANISM: Artificial
<220> FEATURE:
<223> OTHER INFORMATION: Synthesized RNA for a miR-29a

<400> SEQUENCE: 5
uagcaccauc ugaaaucggu ua                                              22

<210> SEQ ID NO 6
<211> LENGTH: 22
<212> TYPE: RNA
<213> ORGANISM: Artificial
<220> FEATURE:
<223> OTHER INFORMATION: Synthesized RNA for a guide strand of a miR-29a

<400> SEQUENCE: 6
accgauuuca gauggugcca ag                                              22

<210> SEQ ID NO 7
<211> LENGTH: 23
<212> TYPE: RNA
<213> ORGANISM: Artificial
<220> FEATURE:
<223> OTHER INFORMATION: Synthesized RNA for a miR-19a

<400> SEQUENCE: 7
ugugcaaauc uaugcaaaac uga                                             23

<210> SEQ ID NO 8
<211> LENGTH: 23
<212> TYPE: RNA
<213> ORGANISM: Artificial
<220> FEATURE:
<223> OTHER INFORMATION: Synthesized RNA for a guide strand of a miR-19a

<400> SEQUENCE: 8
aguuuugcau agauuugcau aag                                             23

<210> SEQ ID NO 9
<211> LENGTH: 22
<212> TYPE: RNA
<213> ORGANISM: Artificial
<220> FEATURE:
<223> OTHER INFORMATION: Synthesized RNA for a guide strand of a miR-183
```

```
                                    (natural type)
<400> SEQUENCE: 9
gugaauuacc gaagggccau aa                                                    22

<210> SEQ ID NO 10
<211> LENGTH: 21
<212> TYPE: RNA
<213> ORGANISM: Artificial
<220> FEATURE:
<223> OTHER INFORMATION: Synthesized RNA for a negative control

<400> SEQUENCE: 10
auccgcgcga uaguacguau u                                                     21

<210> SEQ ID NO 11
<211> LENGTH: 21
<212> TYPE: RNA
<213> ORGANISM: Artificial
<220> FEATURE:
<223> OTHER INFORMATION: Synthesized RNA for a negative control (guide
      strand)

<400> SEQUENCE: 11
uacguacuau cgcgcggauu u                                                     21
```

METHOD FOR DETECTION OF GENES TARGETED BY MICRORNA

TECHNICAL FIELD

The present invention relates to a detection kit for target genes of microRNA (hereinafter, referred to as "miRNA") and a detection method for target genes of miRNA.

The present application claims priority from Japanese Patent Application No. 2010-137924, which is incorporated herein by reference.

BACKGROUND ART miRNA is a single-stranded RNA having about 22 to 25 bases, and is a functional small RNA involved in cellular proliferation, differentiation, and development. The miRNA binds to a 3' untranslated region of mRNA of a gene serving as a target to suppress translation (protein synthesis) of the target genes, thereby being involved in expression control. Hitherto, as many as hundreds of kinds of miRNAs have been identified, and further novel kinds are estimated to be discovered in the future. In recent years, it has been revealed that aberrant expression of the miRNA, for example, is involved in cancer and a variety of other diseases. Accordingly, there have been increasing needs for elucidation of target genes of the miRNA from standpoints of not only basic research but also clinical research. For example, it has been becoming clear that particular miRNAs are expressed at high levels or low levels in certain kinds of cancer cells. However, true target genes of most of the miRNAs are unknown. When cancer is developed because of high level expression of miRNA, a target gene whose protein synthesis is regulated by the miRNA may be estimated to be a gene involved in tumor suppression (tumor suppressor gene). On the other hand, when cancer is developed because of low level expression of miRNA, the target gene of the miRNA may be estimated to be a gene involved in carcinogenesis (oncogene). It is an important task to reveal true target genes of the miRNA, thereby elucidating pathogenic mechanisms of cancer and other diseases and developing molecular-targeted therapeutic drugs therefor.

The miRNA plays an important role in regulation of gene expression. The miRNA is transcribed from DNA in the form of a longer RNA as a precursor in the nucleus and synthesized as pri-miRNA, which is processed by Drosha into pre-miRNA to be transferred to the cytoplasm. The pre-miRNA is processed through action of Dicer into a double-stranded RNA of about 22 to 25 bases, one RNA strand of which is released and the remaining strand of which is incorporated into an RNA-induced silencing complex (RISC complex) to be involved as the miRNA in gene function regulation. It is known that the RISC complex contains an AGO protein. The miRNA in the RISC complex binds to a 3' untranslated region (3'UTR) of mRNA of genes serving as targets. The binding mode of the miRNA is such that not the entirety of its sequence forms a pair but the miRNA binds mainly at a region of about 8 bases at its 5' side (called a seed sequence) and binds in such a form as to contain a mismatch as a whole. This complicates a search for target genes of the miRNA. Some types of target gene prediction software each using a unique algorithm for the target search (miCTS, TargetScan, PicTar, MiRanda, and the like) have been produced. However, target candidate genes selected as a result of the software analysis are tremendous in number, and hence the software analysis at present is far from allowing practical narrowing down of candidate genes.

As a method of narrowing down target genes of the miRNA, there has been reported a method involving purifying mRNA bound to miRNA (Non Patent Literature 1). The method of narrowing down target genes of the miRNA disclosed in Non Patent Literature 1 involves: first inserting a FLAG-tagged AGO gene into cells through infection with a retroviral vector; further transfecting the cells with 3' end biotinylated double-stranded miRNA through use of a transfection reagent; then lysing the cells to produce a cell extract; pulling down an AGO protein complex with anti-FALG antibody beads; next adding a large amount of a FLAG peptide to liberate the AGO protein complex from the anti-FALG antibody beads; subsequently performing an operation of pulling down a biotinylated miRNA complex (containing target gene mRNA) with streptavidin beads; and identifying the thus pulled down mRNA. However, the method is considered to have, for example, the following problems. Laboratories capable of performing the retroviral infection operation are limited. In addition, as many as two gene transfection operations are necessary, resulting in a significant drawback of a reduction in transfection efficiency into cells. Moreover, the mRNA corresponding to the target gene is degraded through the two pull down operations.

CITATION LIST

Non Patent Literature

[NPL 1] Nucleic Acids Research, 2010, Vol. 38, No. 4 e20 doi: 10.1093/nar/gkp1100

SUMMARY OF INVENTION

Technical Problem

An object of the present invention is to provide a detection kit for detecting target genes of miRNA. Another object of the present invention is to provide a method of detecting target genes of miRNA in a simple manner without the need for performing a transfection operation of a gene into cells via a vector.

Solution to Problem

The inventors of the present invention have made extensive studies in order to achieve the objects. As a result, the inventors have found that mRNAs corresponding to target genes of miRNA (hereinafter, mRNA corresponding to target genes is simply referred to as "target gene mRNA") can be easily pulled down by producing a cell extract under mild conditions, adding labeled miRNA to the cell extract, and recovering the labeling substance. Thus, the inventors have completed the present invention, which includes a detection kit for target genes of miRNA, including a cell extraction reagent, and a labeling reagent for miRNA or labeled miRNA, and further including a reaction reagent for the labeling substance for miRNA.

That is, the present invention includes the following.
1. A detection kit for target genes of miRNA, including: a cell extraction reagent; and a labeling reagent for miRNA or labeled miRNA, and further including a reaction reagent for the labeling substance for miRNA.
2. A detection kit for target genes of miRNA according to the above-mentioned item 1, in which the cell extraction reagent includes 0.02 to 1.0 v/v % of a nonionic surfactant and has a pH of 7.3 to 8.0.

3. A detection kit for target genes of miRNA according to the above-mentioned item 2, in which the cell extraction reagent further includes an RNase inhibitor and/or a protease inhibitor.
4. A detection kit for target genes of miRNA according to any one of the above-mentioned items 1 to 3, in which the cell extraction reagent includes 25 mM Tris at a pH of 7.4, 60 mM KCl, 2.5 mM EDTA, 0.05 v/v % NP-40, an RNase inhibitor, and a protease inhibitor.
5. A detection kit for target genes of miRNA according to any one of the above-mentioned items 1 to 4, in which: the labeling substance for miRNA includes biotin; and the reaction reagent for the substance for labeling includes avidin.
6. A detection kit for target genes of miRNA according to any one of the above-mentioned items 1 to 5, further including a reverse transcriptase.
7. A detection method for target genes of miRNA, including: adding labeled miRNA to a cell extract; subjecting the labeled miRNA to a reaction with RNA contained in the cell extract; and recovering the labeled miRNA.
8. A detection method for target genes of miRNA according to the above-mentioned item 7, including the steps of:
1) treating harvested cells or tissue with a cell extraction reagent to prepare a cell extract;
2) adding labeled given miRNA to the cell extract prepared in the step 1);
3) subjecting the labeled given miRNA to a reaction with mRNA contained in the cell extract prepared in the step 1);
4) allowing given mRNA contained in the cell extract prepared in the step 1) and the labeled given miRNA to form a complex together; and
5) subjecting the miRNA labeling substance to a reaction through use of a reaction reagent for the substance for labeling, followed by recovery of the labeled miRNA, to pull down the complex formed in the step 4).
9. A detection method for target genes of miRNA according to the above-mentioned item 7 or 8, in which: the labeled miRNA includes biotinylated miRNA; and the biotinylated miRNA is recovered by subjecting biotin to a reaction with avidin.
10. A detection method for target genes of miRNA according to the above-mentioned item 8 or 9, further including the step of pulling down, from the complex pulled down in the step 5), the mRNA subjected to the reaction with the labeled miRNA, followed by production of cDNA corresponding to target genes of the labeled miRNA through use of a reverse transcriptase.
11. A detection method for target genes of miRNA according to the above-mentioned item 10, further including the step of analyzing the produced cDNA.

Advantageous Effects of Invention

The use of the detection kit for target genes of miRNA of the present invention allows target gene mRNAs for given miRNA to be pulled down. In addition, the kit can be utilized for pulling down not only the target gene mRNAs but also non-mRNA RNAs involved in the complex formation between the miRNA and the target gene mRNA, and proteins specifically expressed in each tissue or each cell and involved in a reaction of the miRNA. The cloning of the target genes and the analysis (identification) of the target genes can be performed by combining this technology for pulling down target gene mRNAs with a cDNA synthesis step, a cloning step, and a detection step.

Further, the use of the detection kit for target genes of miRNA of the present invention obviates the need for the use of a vector such as a retrovirus. Hence, the kit can be easily handled and allows target gene mRNAs to be pulled down in one pull down operation. Accordingly, the target gene mRNAs can be pulled down in a stable state as compared to a conventional technology. In addition, the detection kit for target genes of miRNA of the present invention can be used for not only cultured cells but also specimens obtained from a variety of tissues to pull down target gene mRNAs of given miRNA. Accordingly, the kit is applicable to specimens gained from a variety of fields, such as various cancer tissues, diseased tissues, experimental animals, and plants. Consequently, it is expected that true target genes of miRNAs responsible for a variety of diseases can be easily identified, which may lead to the development of a novel molecular-targeted drug based on such fundamental research.

DESCRIPTION OF EMBODIMENTS

Figure 1:
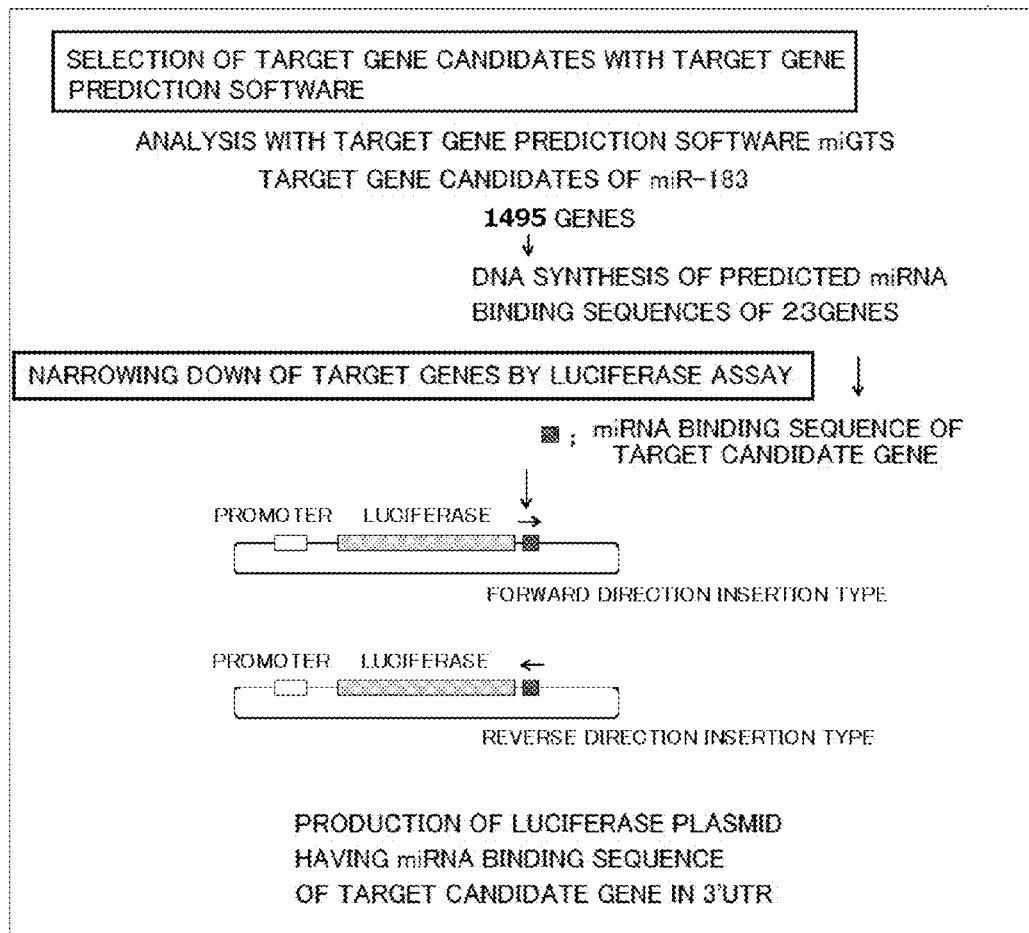
[FIG. 1] A diagram illustrating a flowchart for performing narrowing down of target genes by target gene prediction software and narrowing down by a luciferase reporter assay as preliminary investigations before carrying out the present invention (Reference Examples 1 and 2).

The present invention relates to a detection kit for target genes of miRNA, and also relates to a detection method for target genes of miRNA. In this description, the detection method for target genes of miRNA is first described, and then the detection kit for target genes of miRNA is described.

The detection method for target genes of miRNA includes: subjecting a harvested cell to an extraction treatment under mild conditions to prepare a cell extract; adding labeled miRNA to the cell extract; subjecting the labeled miRNA to a reaction with RNA contained in the cell extract; and recovering the labeled miRNA.

Specifically, the detection method for target genes of miRNA includes the steps of:
1) treating harvested cells or tissue with a cell extraction reagent to prepare a cell extract;
2) adding labeled given miRNA to the cell extract prepared in the step 1);
3) subjecting the labeled given miRNA to a reaction with RNA contained in the cell extract prepared in the step 1);
4) allowing given RNA contained in the cell extract prepared in the step 1) and the labeled given miRNA to form a complex together; and
5) subjecting the miRNA labeling substance to a reaction through use of a reaction reagent for the substance for labeling, followed by recovery of the labeled miRNA, to pull down the complex formed in the step 4).

In the present invention, a specimen for producing the cell extract has only to contain cells, and is not particularly limited. For example, the specimen may be cultured cells, or may be a tissue or cells harvested from a human or a non-human animal. Further, the specimen may be a tissue or cells harvested from a plant. The species of the animal is also not particularly limited as long as the tissue or cells have the possibility of containing miRNA and its target gene mRNA. For example, specific examples of the tissue or cells harvested from a human include blood, urine, saliva, skin, a biopsy sample, and tissues and cells to be gained from various organs. Examples of the tissues to be gained from various organs include a tissue to be obtained postoperatively.

The cell extract may be produced by treating any of various specimens such as the cells and tissues harvested as above with the cell extraction reagent. In this context, miRNA and its target gene mRNA are subjected to a reaction in living cells in ordinary cases, and hence it is important to produce the cell extract in a state that is as close to a living state as possible. Accordingly, it is necessary to produce the cell extract under mild conditions, and it is necessary to use a cell extraction reagent for such conditions.

It is suitable to use, as the cell extraction reagent, a reagent containing 0.02 to 1.0 v/v %, preferably 0.05 to 0.5 v/v %, more preferably 0.05 to 0.1 v/v % of a nonionic surfactant and having a pH of 7.3 to 8.0, preferably a pH of 7.3 to 7.5, more preferably a pH of 7.3 to 7.4. The reagent may further contain an RNase inhibitor and/or a protease inhibitor. As a most preferred composition of the cell extraction reagent, there is given a reagent containing 25 mM Tris (pH 7.4), 60 mM KCl, 2.5 mM EDTA, 0.05 v/v % NP-40, an RNase inhibitor, and a protease inhibitor. Further, with regard to a treatment temperature in the production of the cell extract, the treatment is suitably performed at a temperature at which the activity of a protease contained in the cells is low, for example, 0 to 10° C., preferably 0 to 6° C., more preferably 0 to 4° C. For example, the treatment is suitably performed on ice.

Before treating the various specimens such as the harvested cells and tissues with the cell extraction reagent, the various specimens such as the cells and tissues may be washed with an appropriate solution such as PBS or physiological saline, and may be subjected to treatment such as disruption treatment by means of physical treatment. Further, after the treatment with the cell extraction reagent, the treated specimen may be appropriately subjected to physical treatment such as stirring, shaking, or ultrasonication, centrifugation, additional treatment with any other surfactant appropriate for the tissue, or the like.

In the test method of the present invention, in order to pull down target gene mRNA of given miRNA of interest, it is necessary to label the miRNA. Examples of the labeling substance in this description may include biotin and digoxigenin. It is particularly suitable to label the miRNA with biotin or the like. A method for the labeling of the miRNA, to which a method known per se or any labeling method to be developed in the future is applicable, is not particularly limited. The labeling with the labeling substance in this case may be performed via a linker, or via no linker. For example, it is suitable to phosphorylate the 5' end of the miRNA and biotinylate the 3' end. A thiol group (S—S) may be contained between the 3' end of the miRNA and the labeling substance such as biotin. In order to label the miRNA, a commercially available reagent kit for labeling may be used. The detection kit for target genes of miRNA of the present invention to be described later suitably includes a labeling reagent for miRNA. Further, as described later, the detection kit for target genes of miRNA of the present invention may include given miRNA that has already been labeled, i.e., labeled miRNA. In this case, labeled miRNA can be utilized in the detection method of the present invention, and hence the step of labeling miRNA can be omitted.

In addition, in the detection method for target genes of miRNA of the present invention, it is necessary to subject the labeled given miRNA to a reaction with target gene mRNAs contained in the cell extract. In order for the reaction to proceed more reliably, the labeled miRNA (sense strand) may be converted into double-stranded RNA with an antisense strand. The double strand may be prepared by: producing the antisense strand of the given miRNA; keeping the sense strand and the antisense strand at high temperature, for example, 60 to 75° C., preferably around 70° C.; and then annealing the strands by natural cooling or cooling with a constant-temperature unit. In the case of the double-stranded miRNA, the both strands may be designed so as to each have an overhang of a few bases, for example, 2 bases at the 3' end side. Further, the sense strand and the antisense strand may contain a mismatch structure. In order that the sense strand may bind to target genes mRNA-RICS complex in the cell extract, it is suitable that a strand as a part of the antisense strand contain a mismatch so as to be readily separated from the sense strand.

Next, descriptions are made of the steps of: adding labeled given miRNA to the produced cell extract; subjecting the labeled given miRNA to a reaction with RNA in the cell extract; and allowing given RNA in the cell extract and the labeled given miRNA to form a complex together. These steps are performed in a sequential series. The labeled given miRNA is added to the cell extract, and the mixture is subjected to a reaction at an appropriate temperature and for an appropriate time period, for example, at about 4° C. for 10 to 120 minutes, preferably 20 to 60 minutes, more preferably about 30 minutes, and then further subjected to a reaction at 20 to 35° C., preferably 30° C. for 30 to 180 minutes, preferably 30 to 120 minutes, more preferably 40 to 60 minutes. Thus, the labeled given miRNA can be subjected to a reaction with mRNA in the cell extract, and moreover, the labeled given miRNA and target gene mRNAs present in the cell extract are allowed to form a complex together (labeled miRNA-target gene mRNA complex). It is estimated that, in this process, the labeled miRNA is incorporated into a RISC complex, the strand as apart of the antisense side of double-stranded miRNA is separated from the sense strand to act as mature miRNA, and target gene mRNA is bound to the miRNA-RISC complex.

The step of pulling down the formed complex of miRNA and target gene mRNA (labeled miRNA-target gene mRNA complex) is described. The complex can be pulled down by capturing the labeling substance for the labeled miRNA. For example, when the labeling substance is biotin, a complex of biotinylated miRNA and target gene mRNA of the biotinylated miRNA can be pulled down through a reaction with an avidin compound such as streptavidin immobilized on a solid phase. The solid phase on which streptavidin is immobilized may be beads, a membrane, a glass slide, or a microplate. A material for the solid phase is not particularly limited, and specific examples thereof include a plastic such as agarose or polymethyl methacrylate, and glass. Further, as microbeads, magnetic beads may be used. When the microbeads on which streptavidin has been immobilized are used, a complex containing biotinylated miRNA can be pulled down by recovering the beads. Further, in the case of using the magnetic beads, a non-specific reaction can be suppressed by appropriately selecting their particle diameter and physical properties. For example, as for the particle diameter, in a comparison between particle diameters of 1.0 μm. and 2.8 μm, there is observed such a tendency that the non-specific reaction is more significant in the case of the particle diameter of 1.0 μm. In addition, there is observed such a tendency that the non-specific reaction is more significant in the case of hydrophilic magnetic beads than in the case of hydrophobic magnetic beads. Biotinylated miRNA recovered together with the solid phase such as microbeads can be subjected to the separation of streptavidin and the complex containing biotinylated miRNA by a method known per se, to thereby pull down a biotinylated miRNA-target gene mRNA complex containing biotinylated miRNA. The separation of streptavidin and the complex containing biotinylated miRNA may be performed through, for example, treatment with a high concentration of biotin. When a thiol group (S—S) is contained between the 3' end of miRNA and the labeling substance such as biotin, the separation may be performed by cleaving the S—S bond through treatment with a reducing agent. In order to reduce a non-specific reaction in the separation of streptavidin and the complex containing biotinylated miRNA, the composition of awash solution and the like may be appropriately selected. For example, the use of a wash solution having a high salt concentration can reduce the non-specific reaction. The use of a wash solution having a salt concentration of 100 mM or more, preferably 250 mM or more, more preferably 400 mM or more can suppress the non-specific reaction. The pulled down labeled miRNA-target gene mRNA complex is hereinafter sometimes referred to as "pull-down complex."

In addition, a general extraction method for RNA is applicable to a method of separating target gene mRNAs from the labeled miRNA-target gene mRNA complex. A method known per se or any method to be developed in the future is applicable to the extraction method for RNA. Specific examples thereof include the following methods. The separation may be performed by adding, to the pulled down complex, an RNA extraction solution such as Acid Guanidinium Phenol Chloroform method to denature the proteins. Alternatively, there may be used a commercially available RNA extraction solution such as ISOGEN™ (Nippon Gene Co., Ltd.), TRIzol™ (Invitrogen Corporation), RNAzol™ (COSMO BIO Co., Ltd.), or QIAzol™ (QIAGEN). For example, after adding chloroform to the complex, the mixture is centrifuged at about 4° C. so that a supernatant containing RNA can be obtained. To the supernatant is added isopropyl alcohol to perform ethanol precipitation, and the resultant is centrifuged at about 4° C. Thus, the target gene mRNAs can be separated.

cDNA may be produced from the thus pulled down target gene mRNA by a method known per se using a reverse transcriptase. The produced cDNA of the target gene may be utilized for, for example: (1) amplifying the target gene by a gene amplification method such as a PCR method with a primer capable of amplifying the target gene; (2) directly reading the sequence of the target gene; (3) being converted into double-stranded cDNA and then subjected to cloning to recover target gene cDNA; or (4) being labeled with a fluorescent label to be used as a probe in an array assay. The detection method for target genes of miRNA of the present invention encompasses not only the identification of target genes but also the cloning of the target gene. Cloning the target gene allows the target gene to be analyzed, and also allows a protein synthesized from the target gene to be assayed for its function. In the present invention, the analysis of cDNA encompasses the analysis of an amplified product obtained by subjecting cDNA to gene amplification by employing a technique such as PCR, the analysis of the base sequence of cDNA itself, and the like.

The present invention also provides the detection kit for target genes of miRNA, which is provided for the detection of the target gene of miRNA. The kit includes at least a cell extraction reagent and a labeling reagent for miRNA or labeled miRNA, and further includes a reaction reagent for the labeling substance for miRNA.

It is suitable to use, as the cell extraction reagent included in the kit, a reagent containing 0.02 to 1.0 v/v %, preferably 0.05 to 0.5 v/v %, more preferably 0.05 to 0.1 v/v % of a nonionic surfactant and having a pH of 7.3 to 8.0, preferably a pH of 7.3 to 7.5, more preferably a pH of 7.3 to 7.4. The reagent may further contain an RNase inhibitor and/or a protease inhibitor. As a most preferred composition of the cell extraction reagent, there is given a reagent containing 25 mM Tris (pH 7.4), 60 mM KCl, 2.5 mM EDTA, 0.05 v/v % NP-40, an RNase inhibitor, and a protease inhibitor. The RNase inhibitor may be incorporated at around 80 to 1,000 Units/ml, preferably about 250 Units/ml. Further, the protease inhibitor may be incorporated at around 1 to 100 μg/ml, preferably 1 to 5 μg/ml. As the protease inhibitor, for example, any one of 2 μg/ml aprotinin, pg/ml leupeptin, 2 μg/ml pepstatin A, and 100 μg/ml phenylmethyl-sulfonylfluoride (PMSF) may be appropriately used, and other examples of the protease inhibitor which may be used include protease inhibitors such as antipain, tosyllysine chloromethyl ketone (TLCK), tosylphenylalanine chloromethyl ketone (TPCK), E64, and bestatin.

In the case where the reagent for labeling among the reagents included in the kit is a labeling reagent for miRNA, given miRNA of interest may be labeled with the labeling reagent for miRNA. In this case, the given miRNA may be one not included in the kit, and desired miRNA may be freely labeled. Accordingly, the kit is applicable to a wide range of desired miRNAs. On the other hand, the reagent for labeling may be a reagent containing given miRNA of interest that has already been labeled, i.e., labeled miRNA. In this case, miRNA included in the kit has already been specified, and hence target genes for the labeled miRNA can only be detected, but this is convenient because labeling treatment on the user's part can be omitted. In this context, examples of the labeling substance include biotin, digoxigenin, and a chemical substance to be used for a peptide tag. Of those, in view of easiness of use, biotin or digoxigenin is suitable, and biotin is particularly suitably mentioned.

The reaction reagent for the labeling substance for miRNA included in the kit has only to be a reagent that allows the detection of the labeling substance. For example, when the labeling substance is biotin, the reaction reagent suitably contains an avidin compound, specifically, streptavidin. Biotin and streptavidin physically bind to each other, thereby allowing the biotinylated substance to be captured. For example, immobilizing streptavidin on a solid phase allows the biotinylated substance to be captured on the solid phase. More specifically, the biotinylated substance can be recovered by immobilizing streptavidin on a solid phase such as agarose beads or magnetic beads, and recovering the beads.

The detection kit for target genes of miRNA of the present invention may further include a DNase and a reverse transcriptase. cDNA of the target gene can be produced by: pulling down target gene mRNA through the use of the components of the kit described above; degrading contaminating DNA with the DNase; and then allowing the reverse transcriptase to act on the target gene mRNA.

The produced cDNA may be used for target gene cloning, may be subjected to gene amplification treatment such as PCR, or may be subjected to the analysis of the base sequence of the cDNA itself.

It should be noted that in the detection of target genes of miRNA according to the present invention, the target genes may be narrowed down in advance for given miRNA of interest by target gene prediction software, and narrowing down by a luciferase reporter assay may be performed, before the detection of the target genes of miRNA by the method of the present invention. Further, even when the narrowing down is not performed, target gene mRNAs of miRNA can be easily pulled down by the method of the present invention. As described above, the detection method for target genes of miRNA of the present invention allows not only the identification of target genes but also the cloning of the target gene.

Cloning the target gene allows the target gene to be analyzed, and also allows a protein synthesized from the target genes to be assayed for its function.

EXAMPLES

In order to facilitate the understanding of the present invention, reference examples are shown as preliminary investigations before carrying out the present invention, and the present invention is specifically described by further showing examples, a comparative example, and experimental examples. However, it should be appreciated that the present invention is not limited thereto.

Reference Example 1

Narrowing Down of Target Genes by Target Gene Prediction Software

Hitherto, the inventors of the present invention had used RNA from human lung cancer cells (13 specimens) and normal lung tissues of the same patients (13 specimens) in miRNA arrays and TaqMan real-time quantitative RT-PCR with about 200 kinds of miRNAs. As a result, the inventors had found that the expression of a plurality of miRNAs was increased in lung cancer cells. The inventors focused attention on miR-183, whose expression was remarkably (10 out of the 13 cases) high among those miRNAs. The frequent high level expression of this miRNA in cancer cells led the inventors to consider it important to study the identity of target genes of this miRNA.

Accordingly, the inventors of the present invention decided to first investigate with target gene prediction software. The inventors ran the target gene prediction software miGTS (software produced by Kyowa Hakko Kirin Co., Ltd.) based on the keywords of cell proliferation, apoptosis, and tumor suppressor gene under such conditions that 7 bases of a seed sequence were completely identical and 5 bases or more in a non-seed sequence were identical thereto, and as a result, obtained 1,495 target gene candidates (see FIG. 1). Thus, it was confirmed that it was difficult to narrow down target genes of miRNA through analysis with target gene prediction software.

Reference Example 2

Narrowing Down by Luciferase Reporter Assay

23 Kinds of candidate genes (BTG1, DNMT3A, FAT, PPP2CA, RREB1, RSU1, SEL1L, TNFSF12, TNFRSF9, INFRSF10B, TNFRSF14, SOCS6, SURB7, BCL2L11, LATS2, PDCD4, SMU1, ING3, ST7L, ARHGAP21, BRMS1L, AMID, and VIL2) were appropriately selected from the group consisting of 1,495 target candidate genes selected in Reference Example 1. The inventors decided to perform a luciferase reporter assay with a target sequence (23 bp) located in the 3' untranslated region (3'UTR) of mRNA of each selected target candidate gene (see FIG. 1). VIL2 (Ezrin), which had already been reported as a target gene of miR-183, was used as a positive control.

First, DNA formed of a target sequence found in the 3'UTR of each target candidate gene was synthesized. A plasmid was designed so that the synthesized DNA was located in the 3'UTR of a luciferase gene as a reporter, and a luciferase plasmid having a target sequence of miR-183 incorporated in the forward direction or the reverse direction was produced.

The luciferase plasmid used in this reference example was produced in accordance with the method of Yang et al., i.e., the method described in (Yang Y, Chaerkady R, Beer M A, Mendell J T, Pandey A. Proteomics 2009, 9, 1374-1384). It is estimated that, when the luciferase plasmid having the target sequence incorporated in the forward direction is transfected into cells expressing miR-183, its protein expression is suppressed by miR-183 in the cells, and hence its luciferase activity is reduced as compared to that of the luciferase plasmid having the target sequence incorporated in the reverse direction. Accordingly, each of the produced plasmids (forward direction, reverse direction) was transfected into HEK293 cells (human embryonic kidney cells) expressing miR-183 through the use of a gene transfection reagent Lipofectamine™ 2000 (Invitrogen Corporation), and 24 hours later, the luciferase activity was measured with Dual-Luciferase™ Reporter Assay System (Promega KK).

Figure 2:
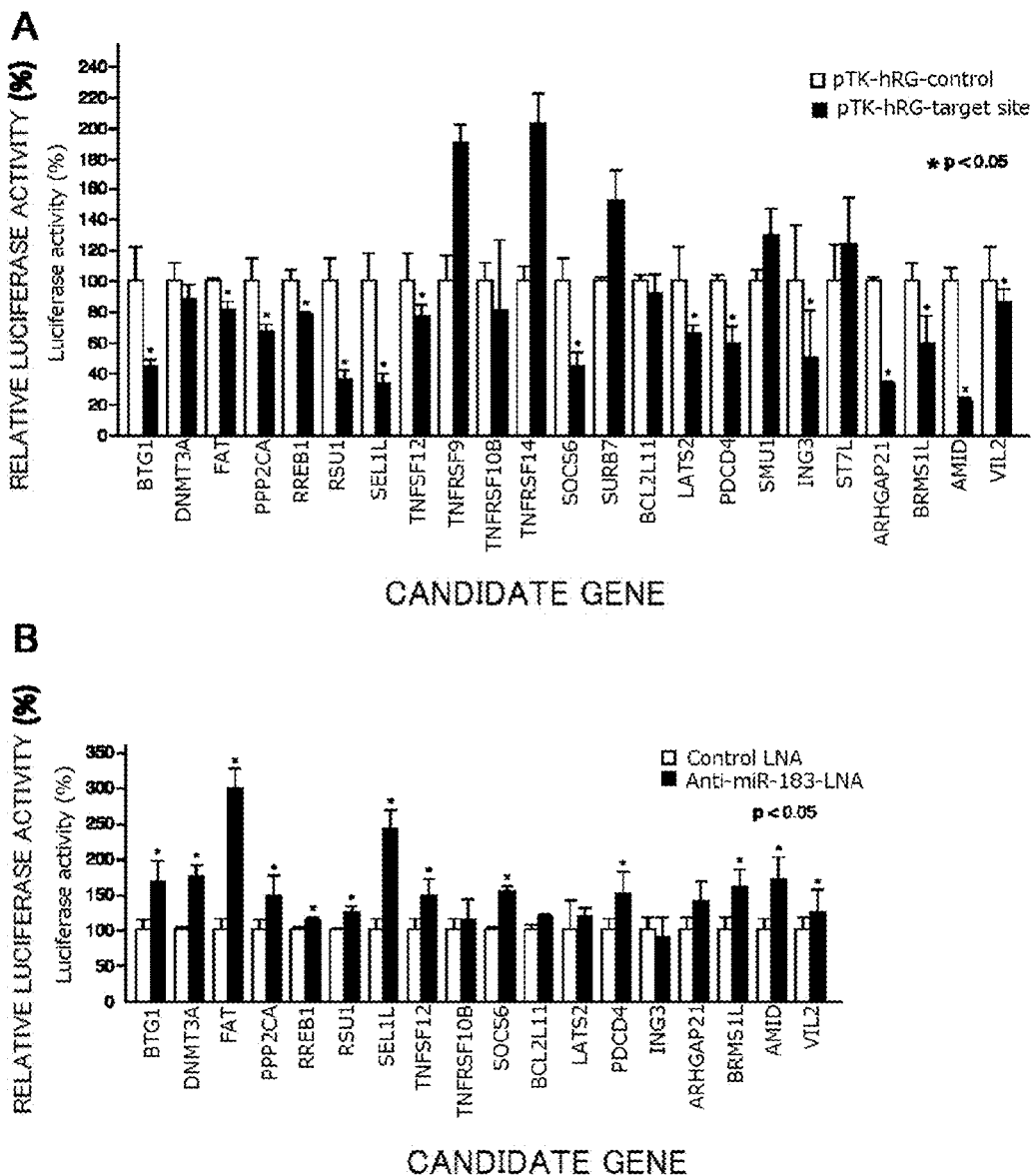
[FIGS. 2] Graphs showing assay results obtained by the luciferase reporter assay (Reference Example 2).

As a result, in each of the candidate genes BTG1, DNMT3A, FAT, PPP2CA, RREB1, RSU1, SEL1L, TNFSF12, INFRSF10B, SOCS6, BCL2L11, LATS2, PDCD4, ING3, ARHGAP21, BRMS1L, AMID, and VIL2, the forward direction insertion type was able to suppress the luciferase activity as compared to the control (target sequence of the reverse direction insertion type) (FIG. 2A). Thus, those candidate genes were considered to have the possibility of certainly being target genes of miR-183.

Following these results, for each of the candidate genes for which the suppression effects had been confirmed, anti-miR-183 LNA (antisense strand nucleotides) was added at the time of the gene transfection of the forward direction insertion type luciferase, to knock down miR-183 in the cells. Then, genes exhibiting reactivation of the luciferase activity (increase in activity) through the knockdown, i.e., BTG1, DNMT3A, FAT, PPP2CA, RREB1, RSU1, SEL1L, TNFSF12, SOCS6, PDCD4, ARHGAP21, BRMS1L, AMID, and VIL2 (14 kinds) were identified as candidate genes (FIG. 2B). It was confirmed that among those candidate genes was included VIL2 (Ezrin), which had already been reported as a target gene of miR-183. Thus, those 14 kinds of candidate genes were shown to have the possibility of certainly being target genes of miR-183. However, even these results were still not enough to clarify whether or not the genes were true target genes.

Comparative Example

Figure 3:
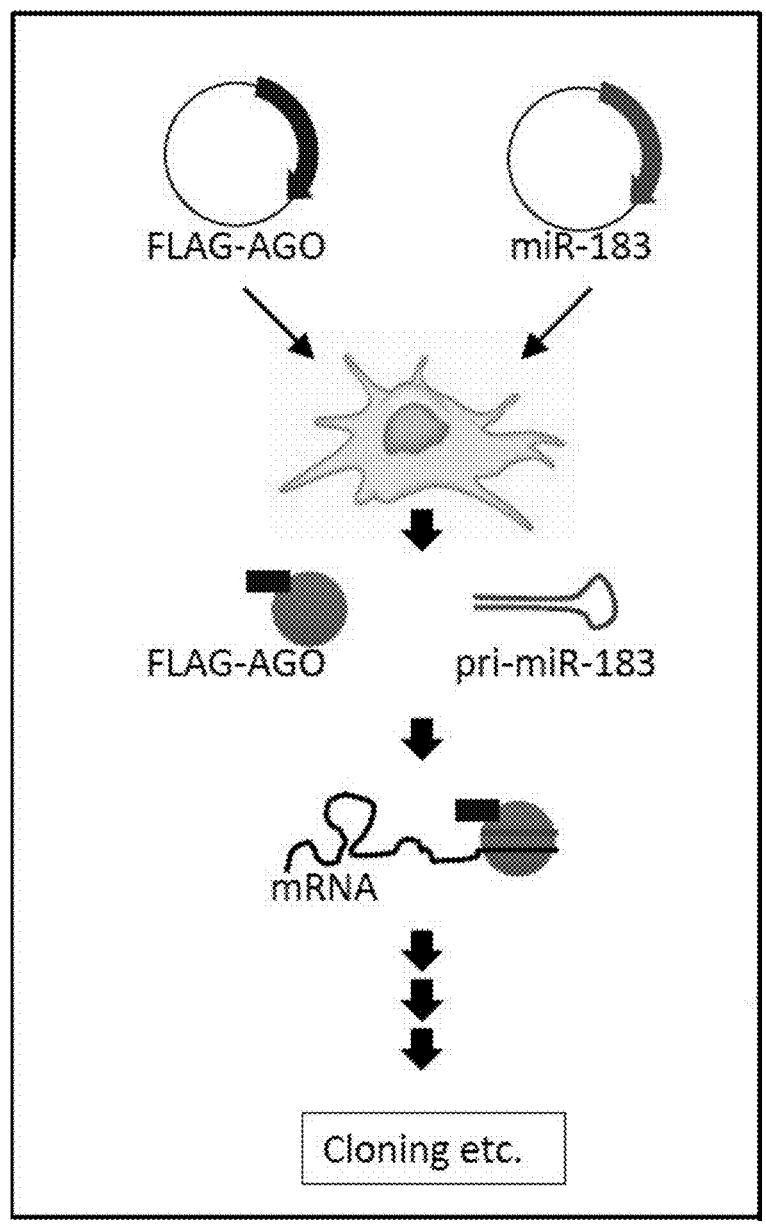
[FIG. 3] A flowchart illustrating a method of pulling down target gene mRNA, involving performing a gene transfection operation into living cells and then pulling down an AGO protein (Comparative Example).

Method of Pulling Down Target Gene mRNA Involving Performing Gene Transfection Operation into Living Cells and then Pulling Down Ago Protein In this comparative example, the inventors tried a method of pulling down target gene mRNA of miRNA involving pulling down an AGO protein as one of the miRNA complex proteins. An miRNA expression vector and a FLAG-tagged AGO expression vector were caused to be strongly expressed in HEK293 cells, and the FLAG-tagged AGO protein was immunoprecipitated with FLAG antibody beads. Thus, target gene mRNA of miRNA pulled down as a complex was separated (see FIG. 3).

Expression vectors for FLAG-tagged AGO1 and AGO2 were constructed by respectively incorporating the cDNAs of AGO1 and AGO2 into FLAG tag expression vectors (pCMV-Tag4A vector: Stratagene). Further, a miR-183 expression vector was constructed by incorporating a pri-miR-183 sequence into a vector for miR expression (pSilencer™ vector). Those expression vectors transfected into HEK293 cells through the use of a transfection reagent (Lipofectamine™ 2000: Invitrogen Corporation). The cells were washed with PBS 48 hours after the transfection, and the cells were recovered with a scraper. To the recovered cells was added a cell extract (25 mM Tris-HCl (pH 7.4), 150 mM KCl, 2 mM EDTA, 0.5% NP-40, 80 U RNase Inhibitor (ABI), 1×Proteinase Inhibitor cocktail (Sigma)), and the mixture was treated on ice with a Vortex mixer for 10 minutes at intervals of 10 seconds to disrupt the cells. After that, the resultant was centrifuged at 4° C. at 12,000 g for 15 minutes, and a supernatant (cell extract) was collected. The expression of the FLAG-AGO protein in the cell extract was confirmed by a Western blot method using a FLAG antibody. Further, with regard to the expression of miR-183, a TaqMan™ miRNA assay confirmed that mature miRNA was expressed from the miR-183 expression vector at a level about several ten times (about 40 times) as high as the original expression level of miR-183 in the cells.

Next, for the cell extract, the FLAG-AGO protein was immunoprecipitated with FLAG antibody beads and collected. After that, mRNAs were purified from the collected immunoprecipitate with an RNA extraction solution ISOGEN™ (Nippon Gene Co., Ltd.), cDNAs were produced with a reverse transcriptase, and the cDNAs were cloned. The resulting 200 clones were assayed for their base sequences. Genes were identified on the basis of the assayed base sequences of the cDNAs, and their 3' untranslated regions were investigated. However, a gene having a miR-183 binding sequence was not able to be obtained. The reason was considered as follows: a large number of target gene mRNAs of miRNAs other than the strongly expressed miR-183 were also pulled down together with the AGO protein. Thus, target gene mRNA of the transfected given miRNA was not able to be pulled down by the method involving pulling down the FLAG-tagged AGO protein in cells.

Example 1

Detection of Target Gene of miRNA Through Use of Biotinylated miRNA (miR-183)

Figure 4:
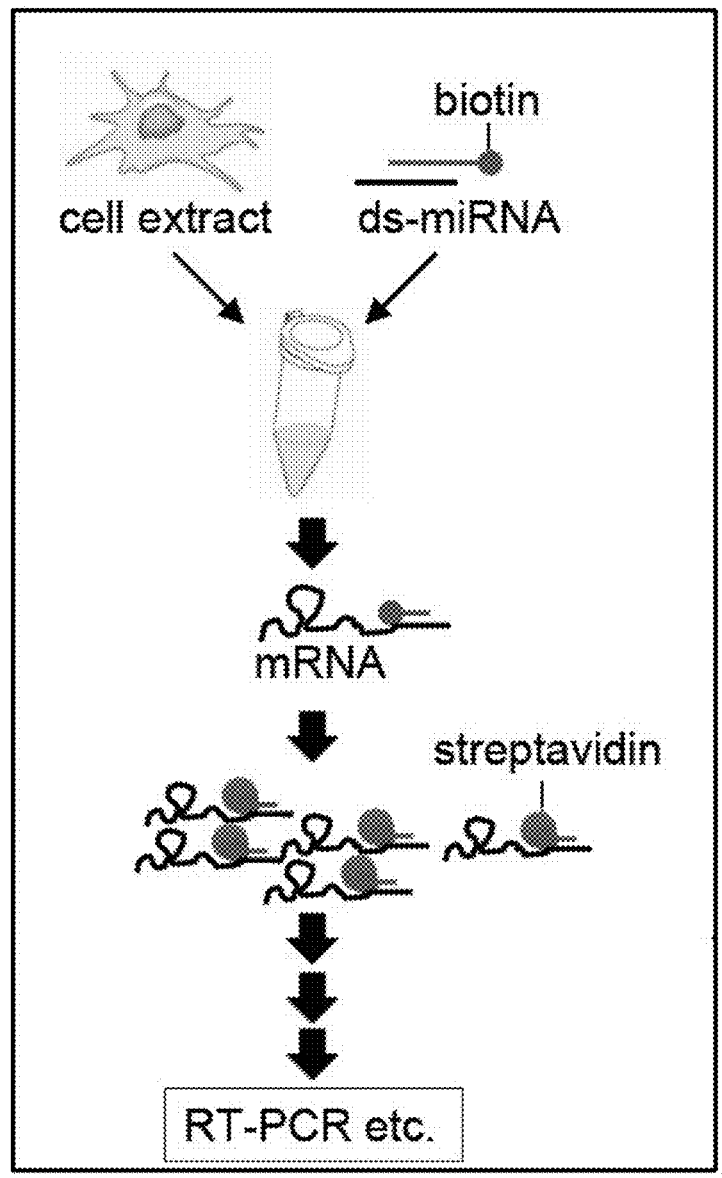
[FIG. 4] A flowchart illustrating a detection method for target genes of miRNA of the present invention, involving using a cell extract (Example 1).

In this example, the inventors aimed at detecting target genes of miRNA (miR-183) in cultured cells. FIG. 4 illustrates a flowchart illustrating a detection method for target genes of miRNA in this example. HEK293 cells were used as the cultured cells.

The inventors thought that, in order to identify true target genes for given miRNA, mRNA physically bound to the given miRNA (in this example, miR-183) had to be captured, and developed a pull down method involving using labeled miRNA. In this example, biotinylated miR-183 and biotinylated let-7b as a control were produced.

1-1) Production of Biotinylated miRNA

Figure 5:
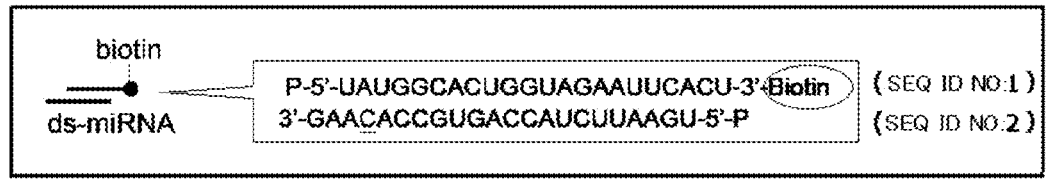
[FIG. 5] A schematic diagram illustrating biotinylated miRNA (double strand) to be used in the detection method for target genes of miRNA of the present invention (Example 1).

For each of miR-183 and let-7b, such a miRNA that the 5' end and the 3' end of the sense strand of the miRNA were phosphorylated and biotinylated, respectively, and such a strand that the 5' end of the antisense strand of the miRNA was phosphorylated were produced. The method for the biotinylation of miRNA was in accordance with the RNA synthesis method of FASMAC Co., Ltd. The biotinylated miRNA and its antisense strand were kept at a temperature of 70° C. in a 100 mM NaCl solution, and then annealed by natural cooling to produce double-stranded miRNA. The both strands were designed so as to each have an overhang of 2 bases as a single strand (as the original sequence) at the 3' end in the double-stranded state. In this case, a strand obtained by inserting a mutation so that a mismatch occurred at the fourth base from the 3' end of the guide strand (SEQ ID NO: 2) was utilized (see FIG. 5).

Base Sequences of miR-183

```
Sense
                                            (SEQ ID NO: 1)
5'-P-UAUGGCACUGGUAGAAUUCACU-biotin-3'

Antisense
                                            (SEQ ID NO: 2)
5'-P-UGAAUUCUACCAGUGCCACAAG-3'
```

1-2) Production of Cell Extract

HEK293 cells (about $2 \times 10^7$ cells: 90-mm culture dish) were washed with PBS, and the cells were recovered with a scraper. To the recovered cells was added a cell extract described below, and the mixture was treated on ice with a Vortex mixer for 10 minutes at intervals of 10 seconds to disrupt the cell. After that, the resultant was centrifuged at 4° C. at 12,000 g for 15 minutes, and a supernatant (cell extract) was collected.

(Composition of Cell Extraction Reagent)

25 mM Tris (pH 7.4)

60 mM KCl 2.5 mM EDTA 0.05% NP-40

80 U RNase Inhibitor (ABI)

1×Proteinase Inhibitor cocktail (Sigma)

1-3) Reaction of Biotinylated Double-Stranded miRNA with RNA in Cell Extract

To the cell extract collected in 2) above were added 10 μl of the biotinylated double-stranded miRNA (1.4 μg/μl) produced in 1) above, and the mixture was subjected to a reaction at 4° C. for 30 minutes, and then at 30° C. for 60 minutes. It was estimated that, in this process, the biotinylated double-stranded miRNA was incorporated into a RISC complex, the antisense strand was separated from the sense strand and released, so that mature miRNA was produced, and target gene mRNA was bound to the miRNA-RISC complex. Thus, a solution containing a biotinylated miRNA-target gene mRNA complex was obtained.

1-4) Pull Down of Biotinylated miRNA-Target Gene mRNA Complex

To the solution containing the biotinylated miRNA-target gene mRNA complex obtained in 3) above were added 50 μl of streptavidin agarose beads (Invitrogen Corporation), and the mixture was treated at 4° C. for 1 hour. The treated liquid was centrifuged at 5,000 revolutions (rpm) for 3 minutes, and the biotinylated miRNA-target gene mRNA complex was pulled down with streptavidin agarose beads. Hereinafter, the biotinylated miRNA-target gene mRNA complex pulled down by this method is sometimes simply referred to as "pull-down complex." After that, 500 μl of a wash solution (20 mM Tris-HCl (pH 7.4), 350 mM KCl, 0.02% NP-40) were used, centrifugation was repeated five times under the same conditions as above, and washing was performed. In order to remove DNA from the pull-down complex pulled down in a precipitate, the precipitate was treated at 37° C. for 30 minutes with a DNA removal reagent kit (100 μl of a 1×DNase buffer, DNase (Sigma, 10 μl)), and then heat-treated at 95° C. for 10 minutes. After that, RNA purification was performed with an RNA extraction solution (ISOGEN™; Nippon Gene Co., Ltd.) to pull down target gene mRNA.

Experimental Example 1-1

Analysis of Target Gene mRNAs by RT-PCR

In this experimental example, analysis was performed for the purpose of verifying whether or not the target gene mRNAs pulled down in Example 1 above corresponded to the genes narrowed down in Reference Examples 1 and 2.

Figure 6:
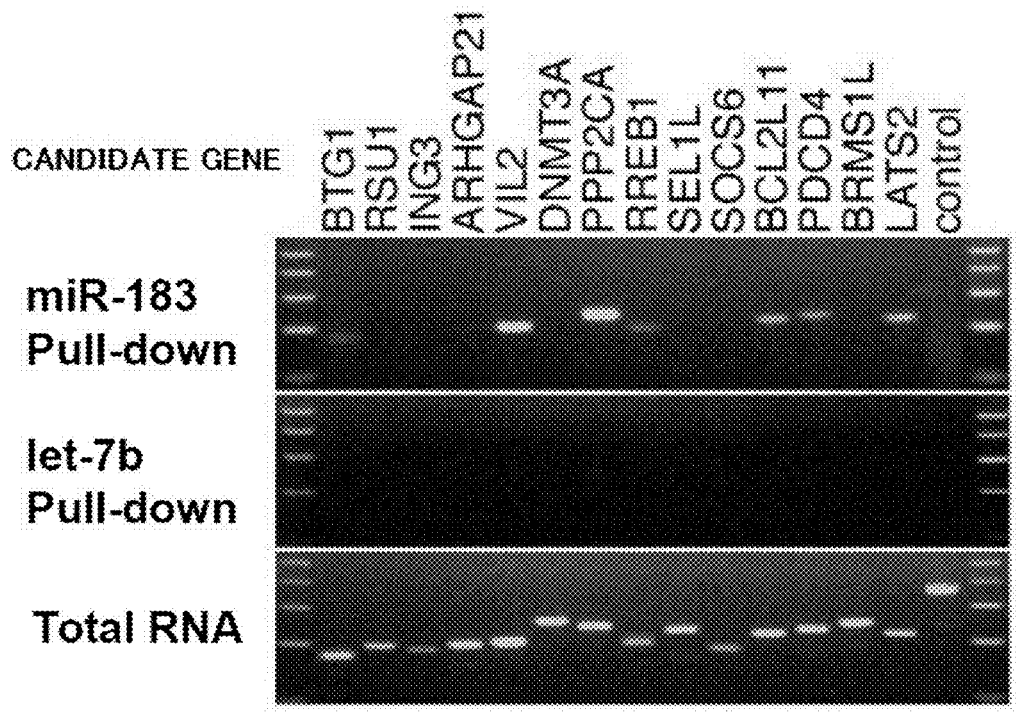
[FIG. 6] Photographs showing results of assaying 14 kinds of target candidate genes of miR-183 obtained in Example 1. The upper photograph of FIG. 6 shows results of assaying target gene mRNAs pulled down through the use of biotinylated miR-183, the middle photograph of FIG. 6 shows results of assaying target gene mRNAs of let-7b pulled down through the use of biotinylated let-7b serving as a negative control, and the lower photograph of FIG. 6 shows results of assaying mRNAs contained in HEK293 cells (human embryonic kidney cells) (Experimental Example 1-1).

In order to confirm whether or not the target gene mRNAs of miR-183 obtained as a result of the analysis with the target gene prediction software miGTS shown in Reference Example 1 and the luciferase assay shown in Reference Example 2 were included in the group of target gene mRNAs pulled down in Example 1, RT-PCR was performed with primers specific for the target candidates, i.e., BTG1, RSU1, ING3, ARHGAP21, VIL2, DNMT3A, PPP2CA, RREB1, SEL1L, SOCS6, BCL2L11, PDCD4, BRMS1L, and LATS2 genes (14 kinds). VIL2, which had already been reported as a target gene of miR-183, was used as a positive control. On the other hand, let-7b as control miRNA is considered as not targeting the 14 kinds of candidate genes because of having a different sequence. Accordingly, an assay was performed using the target gene mRNA of let-7b pulled down from biotinylated let-7b obtained in Example 1 as a control (negative control for miR-183).

cDNAs were produced for the group of target gene mRNAs pulled down in Example 1 with a reverse transcriptase, and an RT-PCR assay was performed with primers specific for the target candidate genes (14 kinds) (the upper photograph of FIG. 6). The amplified products obtained by the RT-PCR were analyzed with agarose gel. As a result, the candidate gene PPP2CA pulled down with biotinylated miR-183 showed a band intensity comparable to that of the positive control VIL2, and then bands were also detected for the BTG1, RREB1, BCL2L11, PDCD4, and LATS2 genes. The target candidate gene mRNA of let-7b pulled down through the use of biotinylated let-7b used as the negative control was subjected to an RT-PCR assay with primers specific for the target candidate genes (14 kinds) in the same manner as above. As a result, no band for any of the genes was detected (middle photograph of FIG. 6). These results showed that mRNAs for 7 kinds out of the 14 kinds of candidate genes narrowed down in Reference Example 2 were pulled down by the pull down technology involving using biotinylated miR-183, suggesting that the 7 kinds of genes were certainly target genes specific for miR-183. The lower photograph of FIG. 6 shows such results that RT-PCR with primers specific for the candidate genes (14 kinds) performed in the same manner as above for mRNAs contained in the HEK293 cell extract used in this experimental example revealed that all the genes were contained therein.

Experimental Example 1-2

Confirmation of Expression Regulation of Target Candidate Gene PPP2CA by miR-183 1

In this experimental example, a Western blot method was employed to confirm whether or not the target candidate gene PPP2CA was actually suppressed by miR-183 in cells.

In order to overexpress miR-183, a pSilencer™ vector having incorporated therein pri-miR-183 was produced. ApSilencer™ vector having incorporated therein miR-1 having a sequence different from that of miR-183, and a pSilencer™ vector were used as negative controls to be compared. HEK293 cells transfected with the respective vectors were cultured for 48 hours.

The respective cells transfected with the respective vectors (1×10^7 cells) were washed with PBS and then transferred to tubes. After centrifugation at 5,000 revolutions (rpm) for 3 minutes, to the resulting cells were added 50 μl of a 2×SDS buffer (100 mM Tris-HCl (pH 6.8), 200 mM dithiothreitol, 4% SDS, 0.2% bromophenol blue, and 20% glycerol), and the mixture was heated for 5 minutes at 100° C. to lyse the cells. 15 μl of the thus treated cell lysate were electrophoresed with 12% SDS-polyacrylamide gel, and proteins were blotted onto a polyvinylidene fluoride (PVDF) membrane with an iBlot™ gel transfer system (Invitrogen Corporation). The transferred PVDF membrane was blocked with a blocking buffer (3% BSA, 0.5% Tween20, and 1×PBS), and then a mouse monoclonal antibody (Abcam plc) against a PPP2CA protein was allowed to react. The PVDF membrane was washed, and then labeling was performed with a Vecstain ABC-AP kit (Vector Laboratories), followed by the addition of CDP-star™ (Roche) as a substrate for alkaline phosphatase. The resulting fluorescence was acquired with a lumino-image analyzer (LAS-1000) (FUJIFILM).

Figure 7:
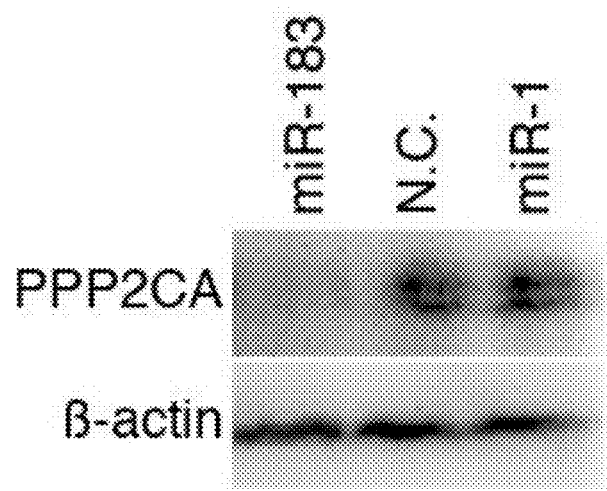
[FIG. 7] Photographs confirming suppressed expression of a target candidate gene PPP2CA caused by miR-183 gene transfection (Experimental Example 1-2).

As a result of the foregoing, it was revealed that the expression of the PPP2CA protein was remarkably suppressed in cells transfected with the pSilencer™ vector having incorporated therein pri-miR-183 for the overexpression of miR-183 (lane 1; miR-183 cells) as compared to the negative controls, i.e., cells transfected with only the pSilencer™ vector (FIG. 7, lane 2; N.C cells) and cells transfected with the pSilencer™ vector having incorporated therein miR-1 (lane 3; miR-1 cells). There results suggested that the candidate gene PPP2CA was one of the true target genes of miR-183.

Experimental Example 1-3

Confirmation of Expression Regulation of Candidate Gene PPP2CA by miR-183 2

Figure 8:
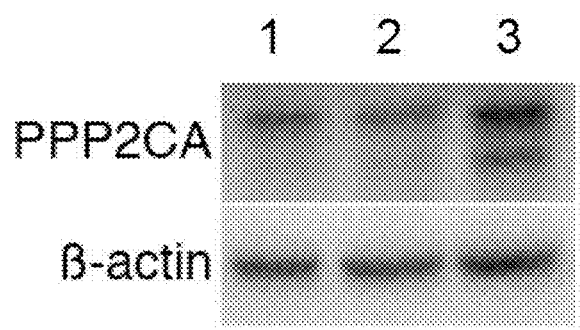
[FIG. 8] Photographs confirming enhanced expression of the target candidate gene PPP2CA caused by antisense miR-183-LNA transfection (Experimental Example 1-3).

In this experimental example, an investigation was made to observe how the expression of the PPP2CA protein from candidate gene PPP2CA mRNA changed when miR-183 in cells was knocked down through transfection with miR-183 antisense. An antisense strand (Locked Nucleic Acid; LNA) for miR-183 was transfected into Lu65a cells (human lung cancer cells). As a negative control, LNA for a GFP gene was transfected into cells. The cells transfected with each LNA were cultured for 48 hours, and the cells were lysed by the same technique as in Experimental Example 2. Each cell lysate was electrophoresed with 12% SDS-polyacrylamide gel by the same technique as in Experimental Example 2, proteins were blotted onto a PVDF membrane, and a mouse monoclonal antibody (Abcam plc) against the PPP2CA protein was allowed to react (FIG. 8). Lane 1 corresponds to untreated Lu65a cells, lane 2 corresponds to cells transfected with LNA for the GFP gene (negative control), and lane 3 corresponds to cells transfected with antisense miR-183 LNA. It was shown that when miR-183 in cells was knocked down with antisense miR-183 LNA, the expression of the PPP2CA protein increased. There results revealed that the candidate gene PPP2CA was one of the true target genes of miR-183.

Experimental Example 1-4

Action of Target Gene PPP2CA of miR-183

Figure 9:
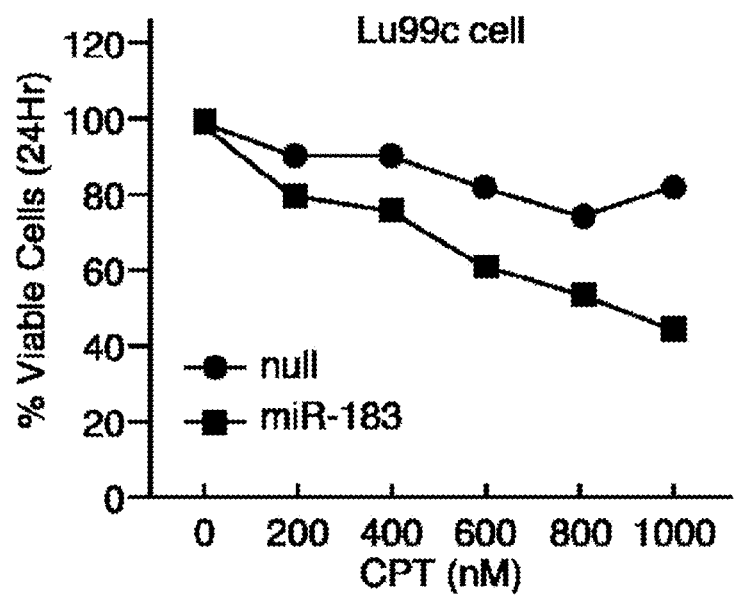
[FIG. 9] A graph confirming the action of miR-183 in the case of inducing DNA damage through the addition of camptothecin (CPT) in cells expressing miR-183 (Experimental Example 1-4).

The target gene PPP2CA suggested as being one of the true target genes of miR-183 was investigated and turned out to be a gene reported to be a subunit of serine-threonine phosphatase, and to be involved in DNA repair and tumor suppression. In view of the fact that the target gene PPP2CA was involved in DNA repair, an investigation was made on the influence of the presence or absence of the target gene PPP2CA on cells by inducing DNA damage through the addition of camptothecin (CPT). An miR-183 expression vector was transfected into an Lu99c lung cancer cell line expressing miR-183 at a low level, and then CPT (final concentration: 0, 200 nM, 400 nM, 600 nM, 800 nM, or 1,000 nM) was added. The number of cells was measured 24 hours after the addition (FIG. 9). The transfection with the miR-183 expression vector suppressed the expression of the target gene PPP2CA, which inhibited DNA repair to promote apoptosis, resulting in a reduction in the percentage of viable cells (FIG. 9).

Figure 10:
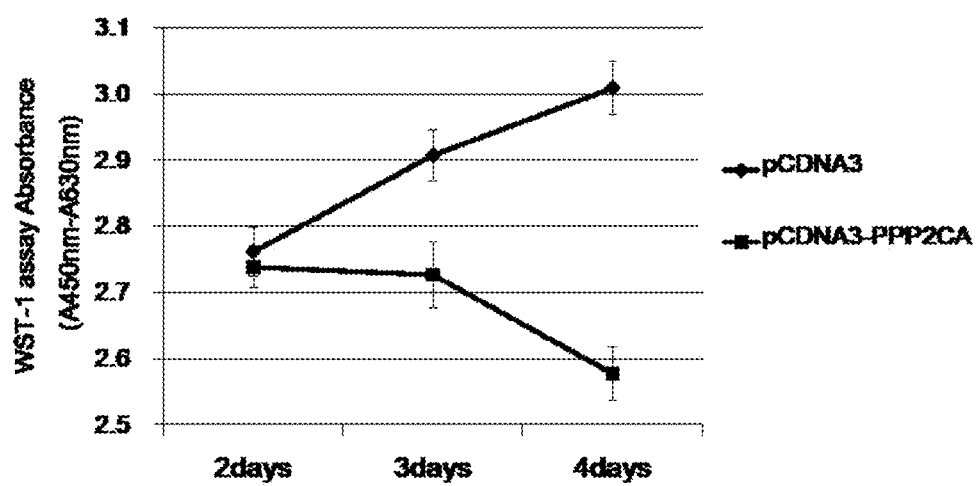
[FIG. 10] A graph confirming the action of miR-183 on the target gene PPP2CA (Experimental Example 1-4).

Further, in view of the fact that the target gene PPP2CA was also involved in tumor suppression, measurement of the number of viable cells was performed after transfecting a target gene PPP2CA expression vector into a Lu65a lung cancer cell line expressing miR-183 at a high level to overexpress the gene. The cells in which forced expression of the target gene PPP2CA was caused were found to reduce in number day by day (FIG. 10). These results suggest that the overexpression of miR-183 in lung cancer inhibits the expression of the target gene PPP2CA at the translational level to cause the lack of DNA stability and tumor suppression function, thereby being involved in carcinogenesis.

The above-mentioned results revealed that the detected target gene PPP2CA of miR-183 exerted an important action on the canceration of cells. The detection method for target genes of miRNA of the present invention is expected to allow a novel target gene of miRNA to be detected in the future, significantly contributing to research for the elucidation of a function thereof.

Example 2

Confirmation of Pull-Down Complex (miR-183)

In this example, for the pull-down complex obtained by the detection method for target genes of miRNA involving using biotinylated miRNA of Example 1, biotinylated miRNA and the AGO2 protein in the pull-down complex were confirmed to verify whether or not the detection method for target genes of miRNA of the present invention was performed functionally.

Biotinylated miR-183 was produced by the same technique as that for the biotinylated miRNA of 1-1) of Example 1, and a cell extract of HEK293 cells was produced by the same technique as that for the cell extract of 1-2) of Example 1. Five tubes in each of which biotinylated double-stranded miR-183 (1,000 μmole) was added to 500 μl of the cell extract were produced, and were each subjected to a reaction at 4° C. for 30 minutes, and then at 30° C. for 60 minutes to provide a solution containing a biotinylated miRNA-target gene mRNA complex. To the solution containing the complex were added streptavidin agarose beads (Streptavidin Mutein Matrix, No. 03 708 152 001: Roche), and each tube was treated at 4° C. for 0 minutes, 2 minutes, 12 minutes, 24 minutes, or 1 hour. A pull-down complex was obtained by the same technique as in 1-4) of Example 1, and washed.

2-1) Confirmation of Recovery of Biotinylated miRNA in Pull-Down Complex

In this experimental example, each of the pull-down complexes obtained through the reactions with streptavidin agarose beads for 0, 2, 12, and 24 minutes, respectively, in Example 2 was treated in accordance with the RNA purification method of 1-4) of Example 1 to pull down RNA. cDNA was synthesized from each RNA sample pulled down through the use of a TaqMan™ MicroRNA Reverse Transcription kit (Applied Biosystems). The detection of biotinylated miR-183 was performed for the resulting cDNA through the use of a TaqMan™ MicroRNA Assay kit (Applied Biosystems) and a Real-Time PCR machine (7300 Real-Time PCR: Applied Biosystems). Each cDNA sample was subjected to the Real-Time PCR in 2 wells.

Figure 11:
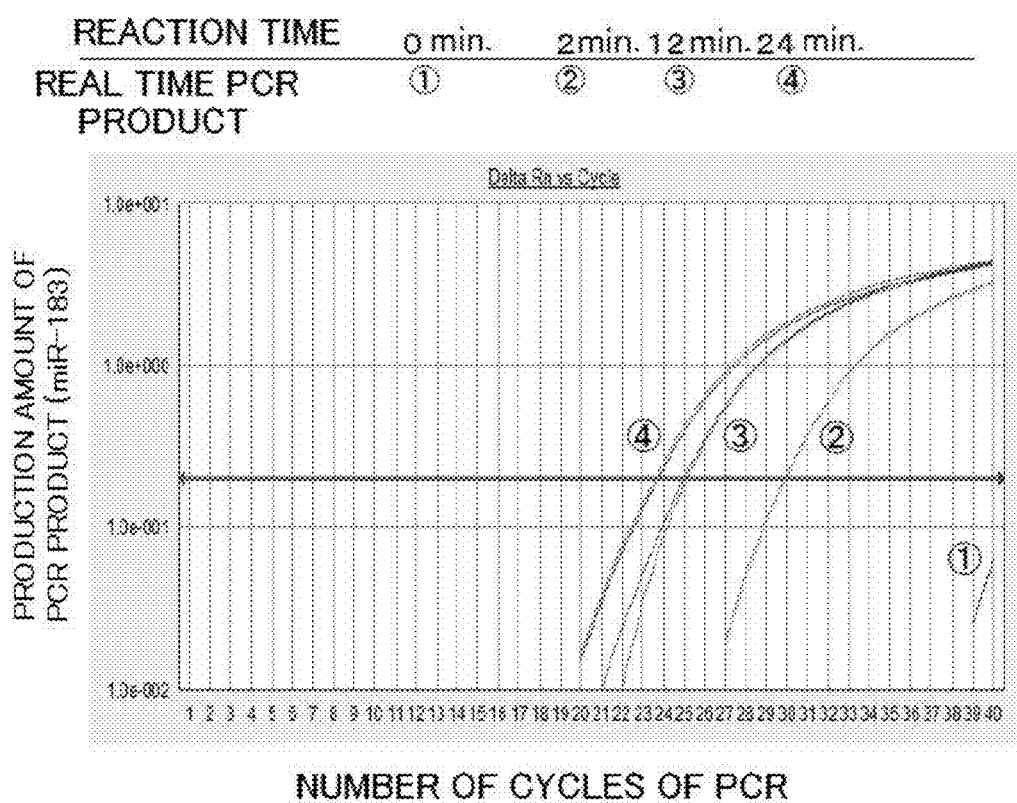
[FIG. 11] A graph showing that biotinylated miRNA can be recovered for a pull-down complex obtained by a detection method for target genes of miRNA involving using biotinylated miRNA (miR-183) (Example 2).

As a result, it was confirmed for each of the cDNA samples that biotinylated miR-183 was detected with a smaller number of cycles of PCR as the reaction time for biotin and streptavidin was longer (FIG. 11). In other words, it was confirmed that as the reaction time for biotin and streptavidin was increased, a larger amount of biotinylated miR-183 was recovered. Thus, it was revealed that the method of the present invention allowed biotinylated miRNA to be recovered.

2-2) Confirmation of AGO2 Protein in Pull-Down Complex

The presence or absence of the AGO2 protein in the pull-down complex of Example 2 was confirmed. The pull-down complex obtained by the reaction with streptavidin agarose beads for 1 hour was used as a sample, and subjected to Western blot against an anti-AGO2 antibody. By the same technique as in Experimental Example 1-2, the sample was electrophoresed with 8% SDS-polyacrylamide gel, proteins were then blotted onto a PVDF membrane and subjected to a reaction through the use of an anti-AGO2 antibody (Anti Human AGO2 monoclonal antibody; Wako Pure Chemical Industries, Ltd., No. 016-20861), an anti-mouse antibody, and a Vecstatin ABC-AP kit (Vector Laboratories), and a fluorescence image was acquired with an image analyzer (LAS-1000; FUJIFILM).

Figure 12:
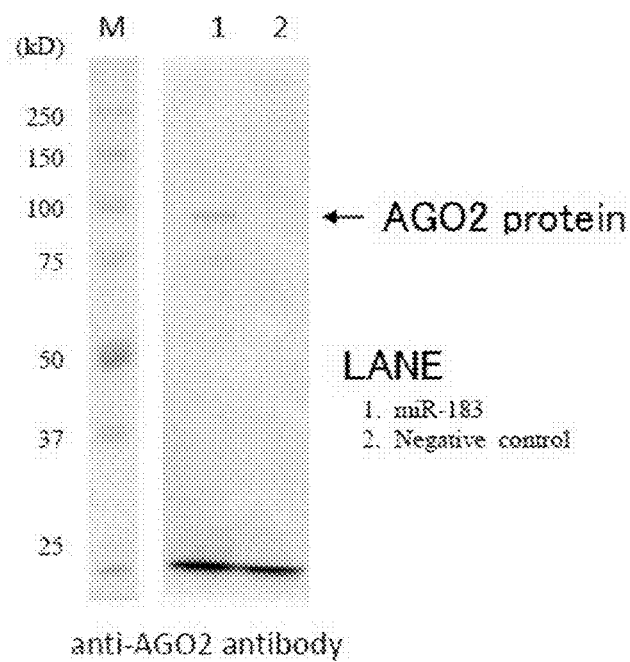
[FIG. 12] An image showing the presence of an AGO2 protein in the pull-down complex obtained by the detection method for target genes of miRNA involving using biotinylated miRNA (miR-183) (Example 2).

As result, the AGO2 protein was not detected for a negative control which was subjected to a reaction in a similar manner but with no addition of biotinylated miR-183 (lane 2), while the AGO2 protein (about 95 kDa) was detected for the pull-down complex obtained by the reaction with the addition of biotinylated miR-183 (lane 1). This revealed that in the detection method for target genes of miRNA of the present invention, biotinylated miRNA certainly formed a complex with the AGO2 protein (FIG. 12).

Example 3

Phosphorylation of Biotinylated miRNA (miR-183)

In this example, the necessity of the phosphorylation of biotinylated miRNA to be used in the detection of target genes of miRNA according to the present invention was confirmed. Such an miRNA that the 5' end of the sense strand of the miRNA miR-183 was phosphorylated was produced (FAS-MAC Co., Ltd., COSMO BIO Co., Ltd.) by the same technique as in the production of biotinylated miRNA of 1) of Example 1. miR-183 whose 5' end was not phosphorylated was produced as a control (COSMO BIO Co., Ltd.). The 3' end of each miR-183 was biotinylated, and the 5' end of the antisense strand was phosphorylated. The biotinylated miRNA and its antisense strand were kept at a temperature of 70° C. in a 100 mM NaCl solution, and then annealed by natural cooling to produce double-stranded miRNA. The base sequences of the sense strand and the antisense strand of the miRNA were designed in accordance with SEQ ID NOS: 1 and 2 in the sequence listing (see FIG. 5) so that each of both strands had an overhang of 2 bases as a single strand (as the original sequence) at the 3' end. A mutation was inserted so that a mismatch occurred at the fourth base from the 3' end of the antisense strand.

Each kind of biotinylated miRNA described above was subjected to the treatments of 1-2) and 1-3) of Example 1. The miRNA was subjected to a reaction with streptavidin agarose beads for 1 hour by the same technique as in Example 2 to afford a pull-down complex. It was confirmed whether or not the AGO2 protein was contained in the pull-down complex by the Western blot method according to the same technique as in 2-2) of Example 2.

Figure 13:
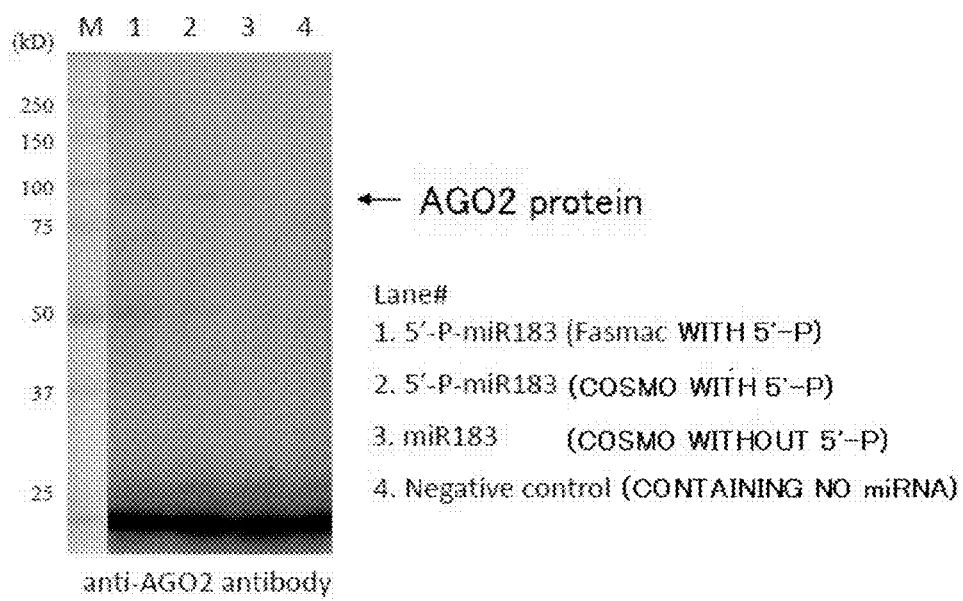
[FIG. 13] An image showing the presence of an AGO2 protein in a pull-down complex obtained by a detection method for target genes of miRNA involving using biotinylated miRNA (miR-183) labeled by 5'-phosphorylation (Example 3).

As a result, as shown in FIG. 13, the AGO2 protein (about 95 kDa) was detected for the pull-down complexes produced with 5' end phosphorylated miR-183 (lane 1 and lane 2), while the AGO2 protein was hardly detected for the pull-down complex using miR-183 whose 5' end was not phosphorylated (lane 3). These results indicate that it is necessary to label biotinylated miRNA to be used in the detection method for target genes of miRNA of the present invention by phosphorylation at the 5' end.

Example 4

Non-Specific Adsorption to Agarose Beads

When a pull-down complex is obtained in the detection of target genes of miRNA according to the present invention, mRNA adsorbs to streptavidin agarose beads in a non-specific manner in some cases even in a negative control system containing no biotinylated miRNA. In this example, the treatments of 1-2) and 1-3) of Example 1 were performed under the state of a negative control containing no biotinylated miRNA. Conditions were confirmed for washing after treatment for a reaction between miRNA and streptavidin agarose beads (Invitrogen Corporation) for obtaining a pull-down complex from the resulting complex by the method of 1-4).

Figure 14:
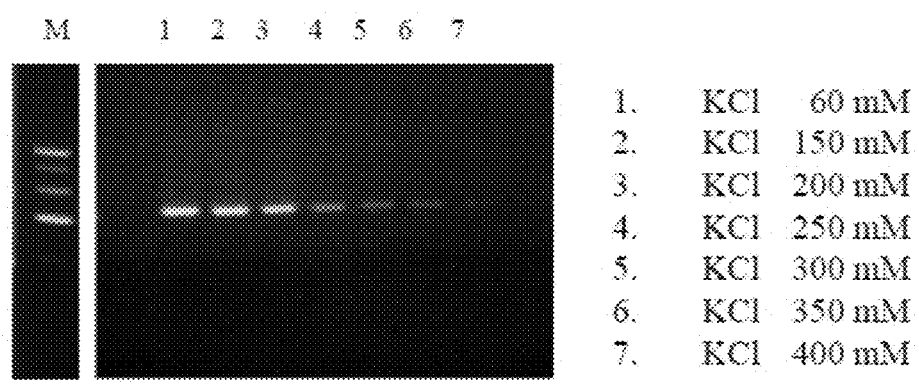
[FIG. 14] An image showing confirmation results on conditions for the suppression of non-specific adsorption of RNA to agarose beads (Example 4).

For a pull-down complex obtained from the negative control system containing no biotinylated miRNA by the method of 1-4) of Example 1, the washing conditions were investigated with 7 kinds of wash solutions shown below. The wash solutions contained mM Tris-HCl (pH 7.4) and 0.5% NP-40 in common, and had concentrations of KCl of 60 mM, 150 mM, 200 mM, 250 mM, 300 mM, 350 mM, and 400 mM, respectively. The pull-down complex was treated with 500 μl of each wash solution for 5 minutes, and then centrifuged at 5,000 revolutions (rpm) for 3 minutes. The resulting precipitate was repeatedly washed and centrifuged a total of five times under the same conditions as above. RNA purification and cDNA synthesis were performed in accordance with 1-4) of Example 1. In order to test non-specific adsorption of mRNA to streptavidin agarose beads, an RT-PCR assay was performed in this case with a primer specific for the BCL2L11 gene as a target candidate gene of miR-183. As a result, it was confirmed that the non-specific adsorption of mRNA reduced when the wash solution had a salt concentration of KCl of 400 mM (FIG. 14).

Example 5

Non-Specific Adsorption Ratio Depending on Magnetic Beads

In this example, differences in non-specific adsorption ratio caused by reaction treatment with streptavidin magnetic beads in place of streptavidin agarose beads were confirmed in obtaining a pull-down complex from the negative control system containing no biotinylated miRNA.

In place of the streptavidin agarose beads in obtaining a pull-down complex by the same technique as in Example 4, 4 kinds of streptavidin magnetic beads (DynaBeads-M280 (particle diameter: 2.8 mm, hydrophobic), DynaBeads-T1 (particle diameter: 2.8 mm, hydrophilic), DynaBeads-M270 (particle diameter: 1.0 mm, hydrophobic), and DynaBeads-C1 (particle diameter: 1.0 mm, hydrophilic) (all manufactured by Invitrogen Corporation)) were used. The solution containing 400 mM. KCl of Example 4 was used as a wash solution. In the pull down and washing, the magnetic beads were recovered with a tube holder provided with a magnet, not by centrifugation. RNA purification and cDNA synthesis were performed in accordance with 1-4) of Example 1. In order to test the non-specific adsorption of mRNA to the various magnetic beads, an RT-PCR assay was performed in this case with primers specific for the VIL2 and BCL2L11 genes as target genes of miR-183, and the E2F6 and SOCS4-1 genes as target genes of let7b.

Figure 15:
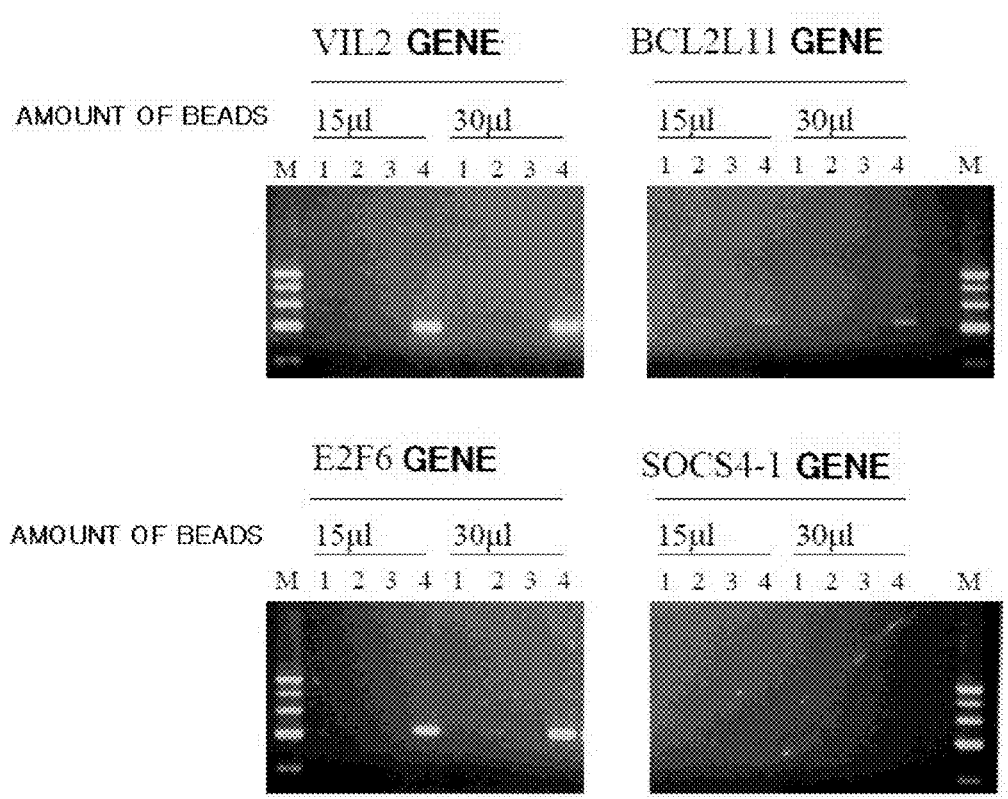
[FIG. 15] Images showing differences in non-specific adsorption ratio depending on magnetic beads (Example 5).

As a result, it was confirmed that non-specific adsorption to hydrophilic beads having small particle diameters occurred at a high ratio (FIG. 15).

Example 6

On Addition of Thiol Group to Biotinylated miRNA (miR-183)

In this example, in a detection method for target genes of miRNA according to the method of the present invention, an investigation was made on the sequence of biotinylated miRNA.

In this example, miRNA containing a thiol group (S—S bond) between the miRNA sequence and the 3' end biotin was produced (FASMAC Co., Ltd.). A biotinylated miRNTarget genes mRNA complex was obtained through the use of miRNA (500 μmole) having the above-mentioned sequence and containing a thiol group, and the complex was pulled down through the use of a solution containing the biotinylated miRNA-target gene mRNA complex and streptavidin beads by the same technique as in 1-4) of Example 1. The complex was washed five times with a wash solution containing 400 mM KCl in the same manner as in Example 5, and then treated with a 100 mM reducing agent dithiothreitol at 42° C. for 10 minutes to perform cleavage treatment for the S—S bond, to thereby liberate the miR-183 complex from the streptavidin beads. The extract containing the liberated miR-183 complex was further subjected to RNA purification and cDNA synthesis by the same technique as in 1-4), and an RT-PCR assay was performed with primers specific for the VIL2 and LATS2 genes as target candidate genes of miR-183.

Figure 16:
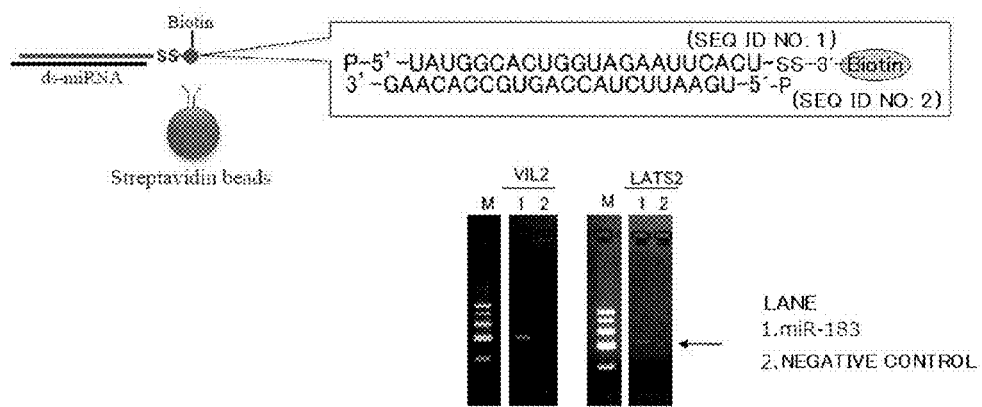
[FIG. 16] Images showing results of the detection of target genes of miR-183 with biotinylated miRNA containing a thiol group (Example 6).

As a result, PCR products of the target genes were detected (lane 1) with the biotinylated miRNA (500 μmole) containing a thiol group of this example, but were not detected with biotin alone (500 pmole) as a negative control. These results revealed that the target genes were able to be pulled down by obtaining a pull-down complex through the use of miRNA containing a thiol group between the miRNA sequence and 3' end biotin, and cleaving the S—S bond with a reducing agent (FIG. 16).

Example 7

Treatment with High Concentration of Biotin (miR-183)

In this example, an investigation was made on liberation of a pull-down complex containing biotinylated miRNA through replacement with a high concentration of biotin in obtaining a pull-down complex from streptavidin beads in a detection method for target genes of miRNA according to the method of the present invention.

In this example, in accordance with the biotinylated miRNA of 1-1) of Example 1, biotinylated miR-183 (500 μmole) and biotin (B4501: Sigma, 500 μmole) as a negative control in place of the biotinylated miR-183 (500 μmole) were subjected to the treatments of 1-2) and 1-3) of Example 1. The resulting complex was treated with streptavidin beads (Streptavidin Mutein Matrix: Roche, or SoftLink Soft Release Avidin Resin: Promega KK) to be pulled down. The complex was washed five times with a wash solution containing 400 mM KCl in the same manner as in Example 5, and then the precipitate was stirred with a 5 mM biotin solution (containing 5 mM biotin and an RNase inhibitor in the wash solution containing 400 mM KCl). Immediately after that, centrifugation was performed at 5,000 revolutions per minute (rpm) for 3 minutes to liberate the biotinylated miR-183 complex from the streptavidin beads. The extract containing the liberated miR-183 complex was subjected to RNA purification and cDNA synthesis by the same technique as in 1-4) of Example 1, and an RT-PCR assay was performed with primers specific for the PDCD4 and LATS2 genes as target candidate genes of miR-183.

Figure 17:
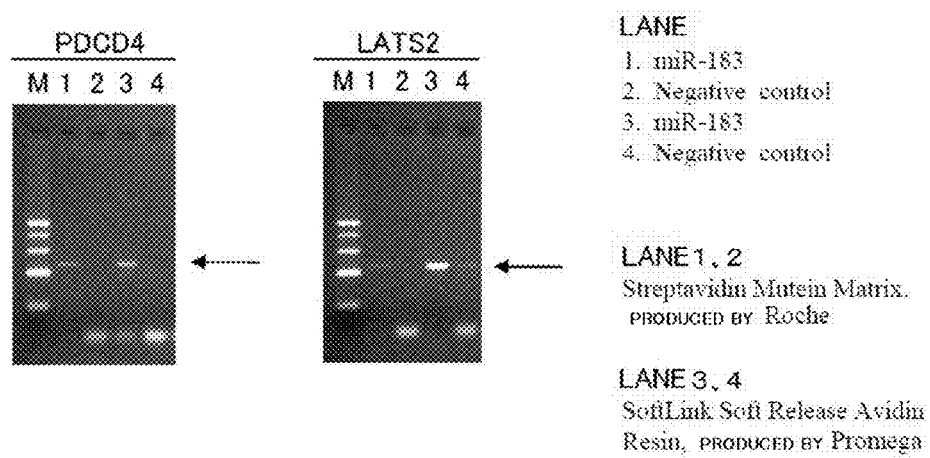
[FIG. 17] Images showing results of the detection of target genes of miR-183 through treatment with a high concentration of biotin (Example 7).

As a result, it was revealed that for any type of streptavidin beads (lanes 1 and 2=Roche, and lanes 3 and 4=Promega KK), the biotinylated miRNA complex was able to be replaced and liberated from the streptavidin beads through treatment with a high concentration of biotin (FIG. 17).

Example 8

Detection of Target Gene of miRNA Through Use of Biotinylated miRNA (Let-7b)

In this example, in the detection method for target genes of miRNA of Example 1, target genes were detected through the use of let-7b as biotinylated miRNA. In accordance with the biotinylated miRNA of 1) of Example 1, biotinylated let-7b in which the sense strand had its 5' end and 3' end modified by phosphorylation and biotin, respectively, and the guide strand had only its 5' end modified by phosphorylation and biotinylated miR-183 as a negative control were synthesized (FASMAC Co., Ltd.). A pull-down complex was obtained by the same technique as in Example 1 through the use of streptavidin beads (Streptavidin Mutein Matrix: Roche), and washed five times with a wash solution containing 400 mM KCl in the same manner as in Example 5. After that, RNA purification and cDNA synthesis were performed from the complex binding to the beads. The resulting cDNA was subjected to an RT-PCR assay with primers specific for the E2F6 and SOCS4-2 genes as target candidate genes of let-7b.

Figure 18:
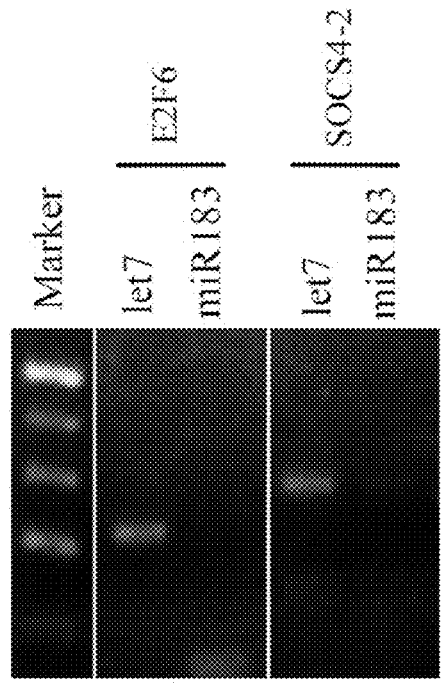
[FIG. 18] Images showing results of the detection of target genes of Let-7b (Example 8).

As a result, it was revealed that E2F6 and SOCS4 as target candidate genes of let-7b were contained in mRNA pulled down with biotinylated let-7b, but were not contained in mRNA pulled down with the negative control (biotinylated miR-183) (FIG. 18). This indicates that the target gene mRNA obtained from the pull-down complex by purification is specific for the biotinylated miRNA used.

Base Sequences of Let-7b

```
Sense
                                      (SEQ ID NO: 3)
5'-P-UGAGGUAGUAGGUUGUGUGGUU-biotin-3'

Antisense
                                      (SEQ ID NO: 4)
5'-P-CCACACAACCUACUACCUUAAG-3'
```

Example 9

Detection of Target Gene of miRNA Through Use of Biotinylated miRNA (Let-7b) (2)

In this example, in the detection method for target genes of miRNA of Example 1, target genes were detected through the use of let-7b as biotinylated miRNA. In this example, the detection was performed by the same technique as in Example 8 except that biotinylated miR-29a was used as a negative control in place of biotinylated miR-183. Also in the case of the biotinylated miR-29a, one in which the sense strand had its 5' end and 3' end modified by phosphorylation and biotin, respectively, and the antisense strand had only its 5' end modified by phosphorylation was produced (FASMAC Co., Ltd.). An RT-PCR assay was performed with primers specific for the PRDM2, E2F2, TUSC2, and SRSF8 genes as target candidate genes let-7b.

Figure 19:
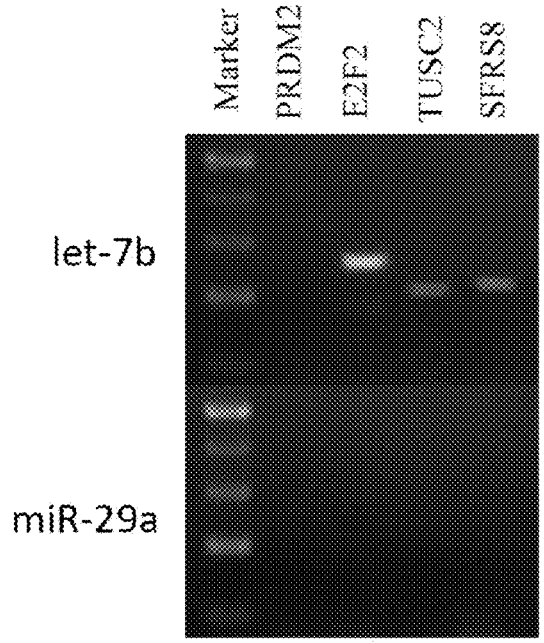
[FIG. 19] Images showing results of the detection of target genes of Let-7b (Example 9).

As a result, it was revealed that E2F2, TUSC2, and SRSF8 as candidate genes of let-7b were contained in mRNA pulled down with biotinylated let-7b, but were not contained in mRNA pulled down with the negative control (biotinylated miR-29a) (FIG. 19). This indicates that the target gene mRNA obtained from the pull-down complex by purification is specific for the biotinylated miRNA used.

Base Sequences of miR-29a

```
Sense
                                      (SEQ ID NO: 5)
5'-P-UAGCACCAUCUGAAAUCGGUUA-biotin-3'

Antisense
                                      (SEQ ID NO: 6)
5'-P-ACCGAUUUCAGAUGGUGCCAAG-3'
```

Example 10

Detection of Target Gene of miRNA Through Use of Biotinylated miRNA (miR-19a) (1)

In this example, in the detection method for target genes of miRNA of Example 1, target genes were detected through the use of miR-19a as biotinylated miRNA. In accordance with the biotinylated miRNA of 1-1) of Example 1, biotinylated miR-19a in which the sense strand had its 5' end and 3' end modified by phosphorylation and biotin, respectively, and the antisense strand had only its 5' end modified by phosphorylation was were synthesized (FASMAC Co., Ltd.). The synthesized biotinylated miR-19a (400 pmole) and biotin (B4501: Sigma, 400 μmole) as a negative control were subjected to the treatments of 1-2) and 1-3) of Example 1. A pull-down complex was obtained from the resulting complex by the same technique as in 1-4) through the use of streptavidin beads (Streptavidin Mutein Matrix: Roche), and washed five times with a wash solution containing 400 mM KCl in the same manner as in Example 5. After that, the precipitate was treated with a 5 mM biotin solution (containing 5 mM biotin and an RNase inhibitor in the wash solution containing 400 mM KCl) at 42° C. for 5 minutes, and centrifuged in the same manner, and the pull-down complex (biotinylated miR-19a) was liberated from the streptavidin beads. RNA purification and cDNA synthesis were performed from the wash solution at the fifth time, the extract obtained with 5 mM biotin, and the remaining streptavidin beads by the same technique as in 1-4) of Example 1, and an RT-PCR assay was performed with primers specific for the SOX4, INHBB, TP531NP1, PTP4A1, TNFAIP3, HIC1, and CNKSR2 genes (7 kinds) as target candidate genes of miR-19a.

Figure 20:
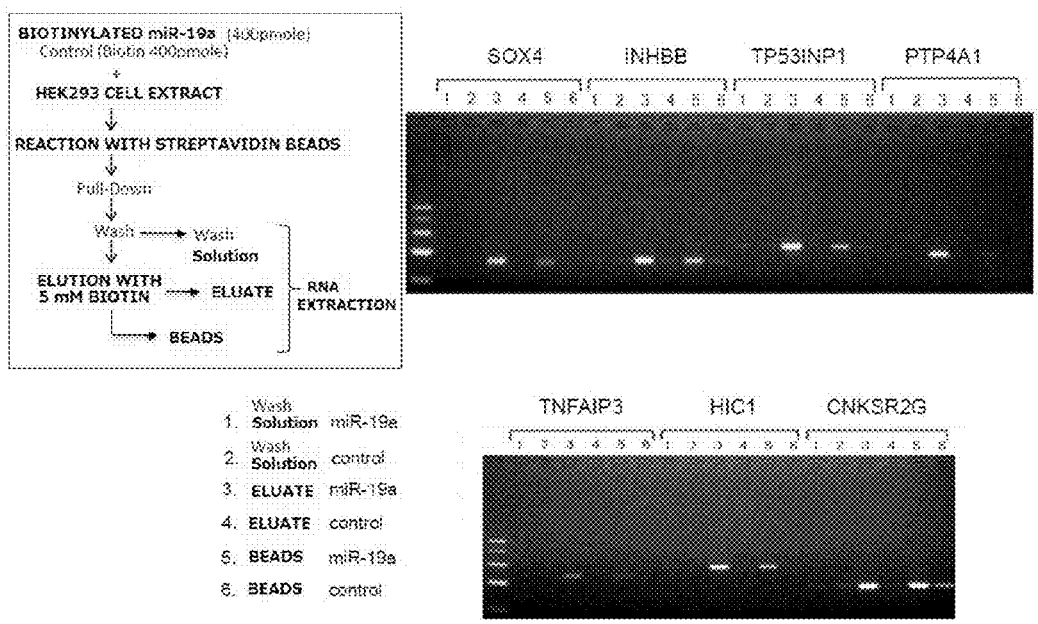
[FIG. 20] A flowchart illustrating a detection process for target genes of miR-19a, and images showing results of the detection of the target genes of miR-19a (Example 10).

As a result, it was revealed that each of the target candidate genes (7 kinds) of miR-19a was present in the extract obtained with 5 mM biotin or on the remaining streptavidin beads in the pull down step with biotinylated miR-19a in contrast to the negative control (FIG. 20). This indicates that the obtained target gene mRNA is specific for the biotinylated miRNA used.

Base Sequences of miR-19a

```
Sense
                                      (SEQ ID NO: 7)
5'-P-UGUGCAAAUCUAUGCAAAACUGA-biotin-3'

Antisense
                                      (SEQ ID NO: 8)
5'-P-AGUUUUGCAUAGAUUUGCAUAAG-3'
```

Example 11

Detection of Target Gene of miRNA Through Use of Biotinylated miRNA (miR-19a) (2)

In this example, target genes were detected through the use of miR-19a as biotinylated miRNA in the detection method for target genes of miRNA of Example 1. In this example, a pull-down complex was obtained by the same technique as in Example 10, and washed in the same manner, i.e., washed five times with a wash solution containing 400 mM KCl in the same manner as in Example 5. After that, RNA purification and cDNA synthesis were performed from the complex binding to the beads. The negative control was also treated by the same technique as in Example 10. The resulting cDNA was subjected to an RT-PCR assay in this example with primers specific for the JAZF1, TNF, SMAD4, HIP1, HIC1, LRP12, TNFRSF12A, TUSC2, and SIVA1 genes (9 kinds) as target candidate genes of miR-19a.

Figure 21:
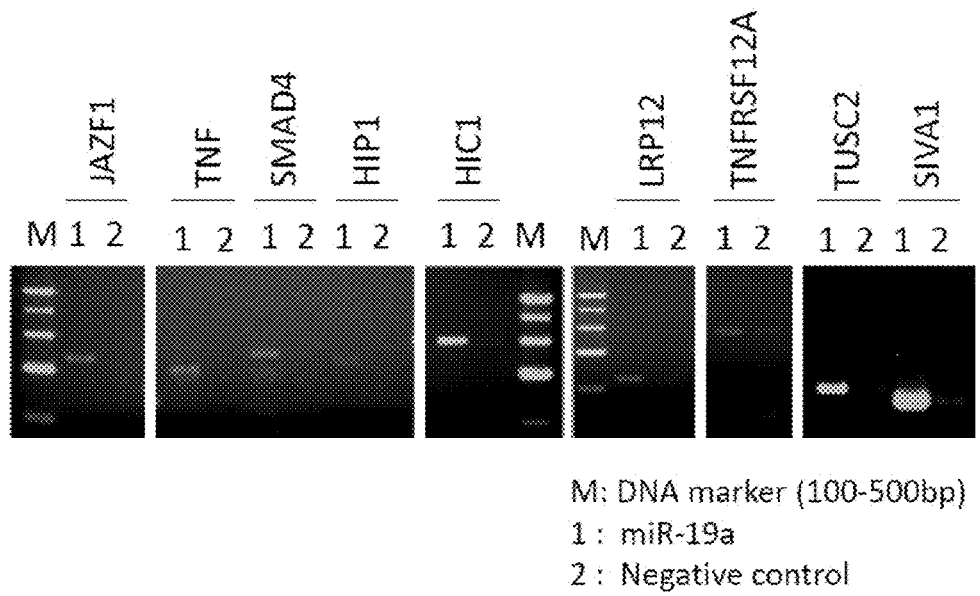
[FIG. 21] Images showing results of the detection of target genes of miR-19a (Example 11).

As a result, it was revealed that the target candidate genes (9 genes) of miR-19a were contained in mRNA pulled down with biotinylated miR-19a, but were not contained in mRNA pulled down with the negative control (FIG. 21). This indicates that target gene mRNA obtained from a pull-down complex by purification is specific for the biotinylated miRNA used.

Example 12

Detection of Target Gene of miRNA with Natural Type miRNA (miR-183)

In this example, a comparative investigation was made on conventional type miRNA and natural type miRNA (mature miRNA type) as biotinylated miRNAs in the detection method for target genes of miRNA of Example 1.

Figure 22:
[FIG. 22] A figure showing different double-stranded RNA sequences of miR-183, and results of the detection of target genes through the use of the sequences (Example 12).
Figure 22:
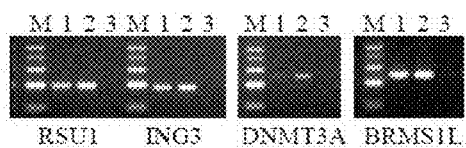

Biotinylated miR-183 (conventional type; containing a 1-base mismatch) used in each of Examples 1 to 5 and 7, biotinylated miR-183 (natural type) as original mature miRNA present in a living body, and biotinylated random sequence double-stranded RNA as a negative control were used. In accordance with the biotinylated miRNA of 1-1) of Example 1, in each miRNA, the sense strand had its 5' end and 3' end modified by phosphorylation and biotin, respectively, and the guide strand had its 5' end modified by phosphorylation. The treatments of 1-2) and 1-3) of Example 1 were performed, and a pull-down complex was obtained from the resulting complex by the same technique as in 1-4) through the use of streptavidin beads (Streptavidin Mutein Matrix: Roche) and washed five times with a wash solution containing 400 mM KCl in the same manner as in Example 5. After that, RNA purification and cDNA synthesis were performed by the same technique as in 1-4) of Example 1, and an RT-PCR assay was performed with primers specific for the VIL2, PPP2CA, RREB1, BCL2L11, PDCD4, LATS2, RSU1, ING3, DNMT3A, and BRMS1L genes (10 kinds) as target candidate genes of miR-183 (FIG. 22).

Base Sequences of miR-183 (Conventional Type)

```
Sense
                                          (SEQ ID NO: 1)
5'-P-UAUGGCACUGGUAGAAUUCACU-biotin-3'

Antisense
                                          (SEQ ID NO: 2)
5'-P-UGAAUUCUACCAGUGCCACAAG-3'
```

Base Sequences of miR-183 (Natural Type)

```
Sense
                                          (SEQ ID NO: 1)
5'-P-UAUGGCACUGGUAGAAUUCACU-biotin-3'

Antisense
                                          (SEQ ID NO: 9)
5'-P-GUGAAUUACCGAAGGGCCAUAA-3'
```

As a result, it was revealed that all of the investigated target candidate genes of miR-183 were contained in the pull-down complexes (biotinylated miR-183) obtained from the conventional type miRNA and the natural type miRNA, but were not contained in the negative control. This suggests that biotinylated conventional type miRNA and biotinylated natural type miRNA can be used in the detection method for target genes of miRNA of the present invention. In consideration of the fact that the sense strands of the conventional type miRNA and the natural type miRNA have completely the same sequence and the sense strand biotinylated miRNA (single strand) incorporated into the RISC is pulled down, it is supported that any of biotinylated miRNA containing a mismatch and biotinylated miRNA containing no mismatch may be used in the detection method for target genes of miRNA of the present invention.

Industrial Applicability

As described in detail above, the use of the detection kit for target genes of miRNA of the present invention allows target gene mRNA for given miRNA to be pulled down. In addition, the kit can be utilized for pulling down not only the target gene mRNA but also non-mRNA RNAs involved in the complex formation between the miRNA and the target gene mRNA, and proteins specifically expressed in each tissue or each cell and involved in a reaction of the miRNA. The cloning of the target gene and the analysis (identification) of the target gene can be performed by combining this technology for pulling down target gene mRNA with a cDNA synthesis step, a cloning step, and a detection step.

The detection kit for target genes of miRNA of the present invention is applicable to a series of kit products such as a kit for pulling down target gene mRNAs, a cloning kit for target genes, and a detection kit for target genes, and hence the target gene of given miRNA can be elucidated. Thus, the kit is expected to be utilized by miRNA researchers in not only clinical fields such as diseases but also a wide range of fields including basic research such as iPS cell research.

In particular, the method of the present invention allows direct pull down of target gene mRNA from not only cultured cells but also a variety of tissues. Accordingly, the method is applicable to a variety of fields such as various cancer tissues, diseased tissues, experimental animals, and plants. As a result, it is expected that true target genes of miRNA responsible for a variety of diseases can be easily identified, which may lead to the development of a novel molecular-targeted drug based on such fundamental research.

The invention claimed is:

1. A detection method for the presence of an RNA of target genes of microRNA in a cell extract, wherein the RNA of target genes of microRNA comprises mRNA, non-mRNA, or a combination thereof of the target genes of microRNA, said method comprising:

adding a labeled microRNA to a cell extract under conditions sufficient to form a complex between the labeled microRNA and the RNA of target genes of microRNA when the RNA of target genes of microRNA is present in the cell extract, wherein the labeled microRNA is a double-stranded microRNA with a labeled sense strand, and wherein said complex comprises an RNA-induced silencing complex (RISC), and detecting the presence of the RNA of target genes of microRNA in the cell extract by analyzing for formation of the complex between the labeled microRNA and the RNA of target genes of microRNA.

2. The detection method for the presence of RNA of the target genes of microRNA according to claim 1 further comprising the steps of:
   (a) harvesting a cell or tissue; and
   (b) treating the harvested cell or tissue with a cell extraction reagent to produce the cell extract.

3. The detection method for the presence of RNA of the target genes of microRNA according to claim 1, wherein the labeled microRNA comprises biotinylated microRNA.

4. The detection method for the presence of RNA of the target genes of microRNA according to claim 1 further comprising the step of:
   isolating the complex between the labeled microRNA and the RNA of target genes of microRNA; and
   producing a cDNA corresponding to target genes of the labeled microRNA using the RNA of the target genes of microRNA and a reverse transcriptase.

5. The detection method for the presence of RNA of the target genes of microRNA according to claim 4 further comprising the step of analyzing the produced cDNA.

6. The detection method for the presence of RNA of the target genes of microRNA according to claim 3 further comprising the steps of recovering the biotinylated microRNA by binding the biotinynated microRNA to avidin.

7. The detection method for the presence of RNA of the target genes of the microRNA according to claim 2 further comprising the step of identifying the RNA of target genes of microRNA.

8. A method for detecting for the presence of an RNA of target genes of microRNA in a cell extract, wherein the RNA of target genes of microRNA comprises mRNA, non-mRNA, or a combination thereof of the target genes of microRNA, said method comprising:

adding a labeled microRNA to a cell extract under conditions sufficient to form a complex between the labeled microRNA and the RNA of target genes of microRNA when the RNA of target genes of microRNA is present in the cell extract, wherein the labeled microRNA is a double-stranded microRNA with a labeled sense strand; and determining the presence of the RNA of target genes of microRNA in the cell extract by analyzing for formation of the complex between the labeled microRNA and the RNA of target genes of the label microRNA.

9. The method for detecting for the presence of an RNA of target genes of microRNA in a cell extract according to claim 8 further comprising the steps of:
   (a) harvesting a cell or tissue; and
   (b) treating the harvested cell or tissue with a cell extraction reagent to produce the cell extract.

10. The method for detecting for the presence of an RNA of target genes of microRNA in a cell extract according to claim 8, wherein the labeled microRNA comprises biotinylated microRNA.

11. The method for detecting for the presence of an RNA of target genes of microRNA in a cell extract according to claim 8 further comprising the step of:

isolating the complex between the labeled microRNA and the RNA of target genes of microRNA; and producing a cDNA corresponding to target genes of the labeled microRNA using the RNA of the target genes of microRNA and a reverse transcriptase.

12. The method for detecting for the presence of an RNA of target genes of microRNA in a cell extract according to claim 11 further comprising the step of analyzing the produced cDNA.

13. The method for detecting for the presence of an RNA of target genes of microRNA in a cell extract according to claim 11 further comprising the steps of recovering the biotinylated microRNA by binding the biotinynated microRNA to avidin.

14. The method for detecting for the presence of an RNA of target genes of microRNA in a cell extract according to claim 8, wherein said complex between the labeled microRNA and the RNA of target genes of microRNA comprises a microRNA-RISC complex.

15. The method for detecting for the presence of an RNA of target genes of microRNA in a cell extract according to claim 8 further comprising the step of identifying the RNA of target genes of microRNA.

* * * * *